(12) United States Patent
Chung et al.

(10) Patent No.: US 12,077,599 B2
(45) Date of Patent: Sep. 3, 2024

(54) ANTI-ROS1 ANTIBODY AND USE THEREOF

(71) Applicants: Seoul National University R&DB Foundation, Seoul (KR); NATIONAL CANCER CENTER, Goyang-si (KR); THE ASAN FOUNDATION, Seoul (KR); University of Ulsan Foundation For Industry Cooperation, Ulsan (KR)

(72) Inventors: Junho Chung, Seongnam-si (KR); Eugene C. Yi, Seoul (KR); Ji Eun Kim, Seoul (KR); Hwa Kyoung Lee, Seoul (KR); Junyeong Jin, Gwacheon-si (KR); Jong Bae Park, Goyang-si (KR); Hyori Kim, Seoul (KR)

(73) Assignees: SEOUL NATIONAL UNIVERSITY R&DB FOUNDATION, NATIONAL CANCER CENTER, Goyang-si (KR); THE ASAN FOUNDATION, UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 1133 days.

(21) Appl. No.: 16/767,245

(22) PCT Filed: Mar. 6, 2018

(86) PCT No.: PCT/KR2018/002655
§ 371 (c)(1),
(2) Date: May 27, 2020

(87) PCT Pub. No.: WO2019/107671
PCT Pub. Date: Jun. 6, 2019

(65) Prior Publication Data
US 2023/0242670 A1    Aug. 3, 2023

Related U.S. Application Data

(60) Provisional application No. 62/591,974, filed on Nov. 29, 2017.

(51) Int. Cl.
*C07K 16/40* (2006.01)
*G01N 33/574* (2006.01)

(52) U.S. Cl.
CPC ....... *C07K 16/40* (2013.01); *G01N 33/57423* (2013.01); *C07K 2317/24* (2013.01); *C07K 2317/52* (2013.01); *C07K 2317/55* (2013.01); *C07K 2317/565* (2013.01); *C07K 2317/622* (2013.01)

(58) Field of Classification Search
CPC .............. C07K 16/40; C07K 2317/24; C07K 2317/52; C07K 2317/55; C07K 2317/565; C07K 2317/622; G01N 33/57423
USPC .................................................... 424/133.1
See application file for complete search history.

(56) References Cited

U.S. PATENT DOCUMENTS

| 2011/0008347 | A1* | 1/2011 | Ullrich ................. C12N 9/1205 424/139.1 |
|---|---|---|---|
| 2012/0237530 | A1 | 9/2012 | Matsuda et al. |
| 2013/0336923 | A1 | 12/2013 | Marasco et al. |
| 2014/0243332 | A1 | 8/2014 | Davare et al. |
| 2015/0064187 | A1 | 3/2015 | Yokosaki et al. |

FOREIGN PATENT DOCUMENTS

| CN | 106978401 | 7/2017 |
|---|---|---|
| KR | 10-2016-0064781 | 6/2016 |
| KR | 10-1736420 | 5/2017 |
| WO | 2011-049082 | 4/2011 |
| WO | 2011-162295 | 12/2011 |
| WO | 2013-183578 | 12/2013 |
| WO | 2014-016737 | 1/2014 |
| WO | 2017-037220 | 3/2017 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
KIPO, PCT Search Report & Written Opinion of PCT/KR2018/002655 dated Sep. 10, 2018.
Hwa Kyoung Lee et al., "A point mutation in the heavy chain complementarity-determining region 3 (HCDR3) significantly enhances the specificity of an anti-ROS1 antibody", Biochemical and Biophysical Research Communications 493 (2017) 325-331.
C.F. Barbas, Phage Display: a Laboratory Manual, Cold Spring Harbor Laboratory Press, Cold Spring Harbor, NY, 2001 (9.102~9.107 & 10.2~10.9).
Sunyoung Park et al., "A sensitive enzyme immunoassay for measuring cotinine in passive smokers", Clinica Chimica Acta 411 (2010) 1238-1242.
Hyori Kim et al., "Application of bispecific antibody against antigen and hapten for immunodetection and immunopurification", Exp. Mol. Med. 45 (2013) e43.
Yujean Lee et al., "An antibody reactive to the Gly63-Lys68 epitope of NT-proBNP exhibits O-glycosylation-independent binding", Exp. Mol. Med. 46 (2014) e114.
Otmane Boussif et al., "A versatile vector for gene and oligonucleotide transfer into cells in culture and in vivo: polyethylenimine", Proc. Natl. Acad. Sci. U. S. A. 92 (1995) 7297-7301.
Jinlong Yin et al., "Correction: Pigment Epithelium-Derived Factor (PEDF) Expression Induced by EGFRvill Promotes Self-renewal and Tumor Progression of Glioma Stem Cells", PLoS Biol. 14 (2016) e1002367.

(Continued)

*Primary Examiner* — Yan Xiao
(74) *Attorney, Agent, or Firm* — LEX IP MEISTER, PLLC

(57) ABSTRACT

The present invention relates to an anti-ROS1 antibody improved in specificity for ROS1 and a use thereof and, more particularly, provides an anti-ROS1 antibody or an antigen-binding fragment thereof and a use thereof in cancer diagnosis.

12 Claims, 6 Drawing Sheets

Specification includes a Sequence Listing.

(56) References Cited

OTHER PUBLICATIONS

Jinlong Yin, "CPEB1 modulates differentiation of glioma stem cells via down-regulation of HES1 and SIRT1 expression", Oncotarget 5 (2014) 6756-6769.
Andrej Shevchenko et al., "In-gel digestion for mass spectrometric characterization of proteins and proteomes", Nat. Protoc. 1 (2006) 2856-2860.
NovusBio. Product Datasheet ROS antibody NBP2-30090(Oct. 16, 2017).
Lukas Bubendorf et al., "Testing for ROS1 in non-small cell lung cancer: a review with recommendations", Virchows Arch. 2016, 469:489-503.
ROS Antibody NBP2-30090,novusbio, Oct. 2017, https://www.novusbio.com/PDFs2/NBP2-30090.pdf.
ROS Polyclonal Antibody, ThermoFisher, 2015 https://assets.thermofisher.com/TFS-Assets/LSG/SDS/PA130318_MTR-JPLT_BE.pdf; https://www.thermofisher.com/antibody/product/ROS1-Antibody-Polyclonal/PA1-30318.

\* cited by examiner

[FIG. 1a]
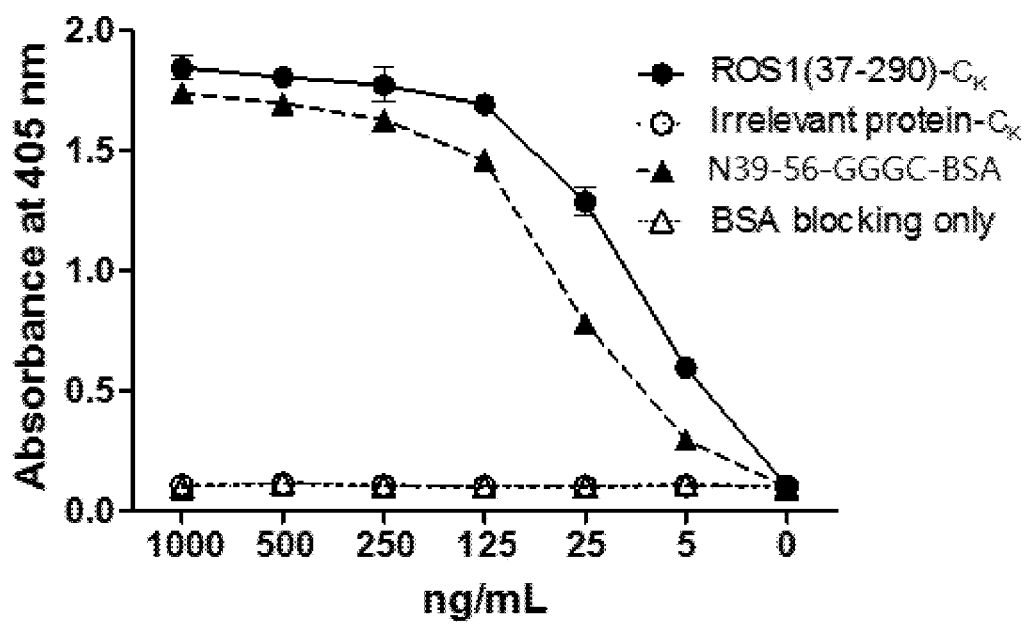
[FIG. 1b]
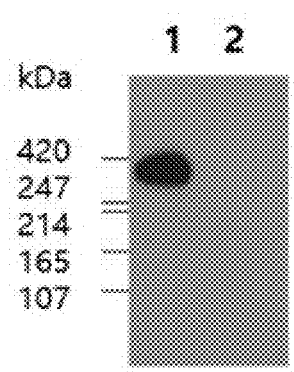

【FIG. 1c】
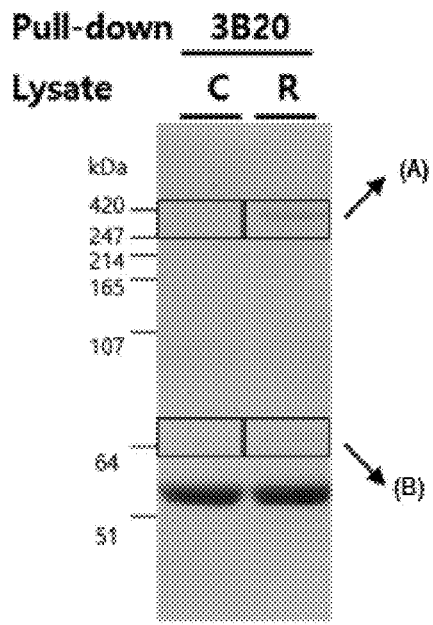
【FIG. 2a】
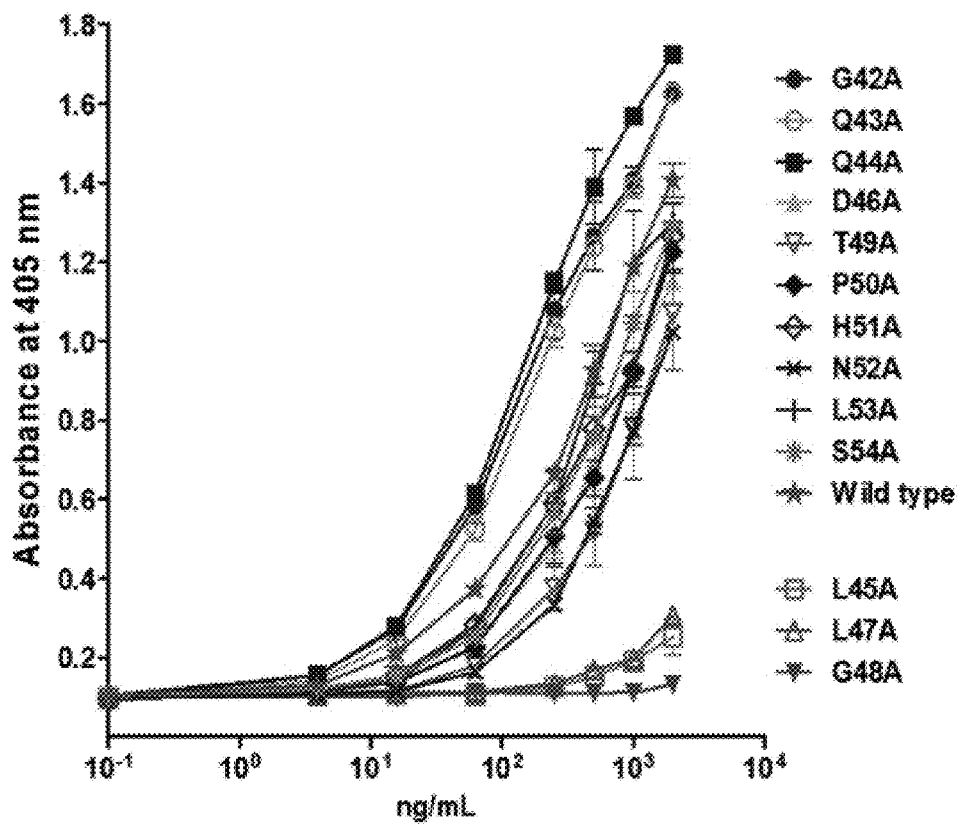

[FIG. 2b]
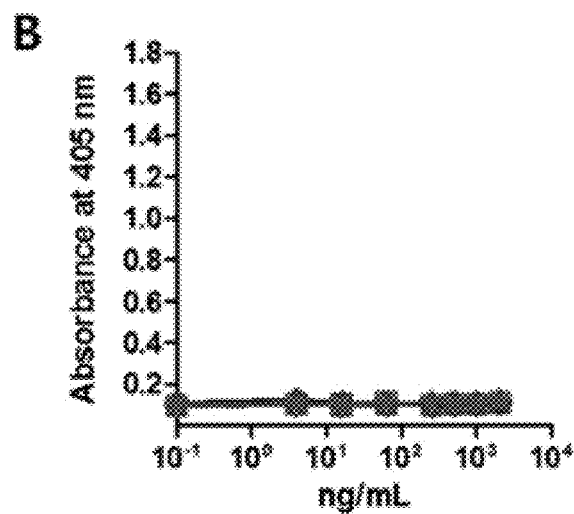
[FIG. 2c]
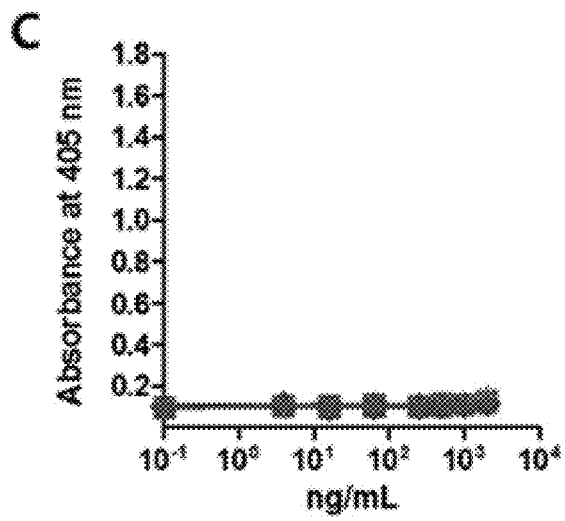

[FIG. 3a]
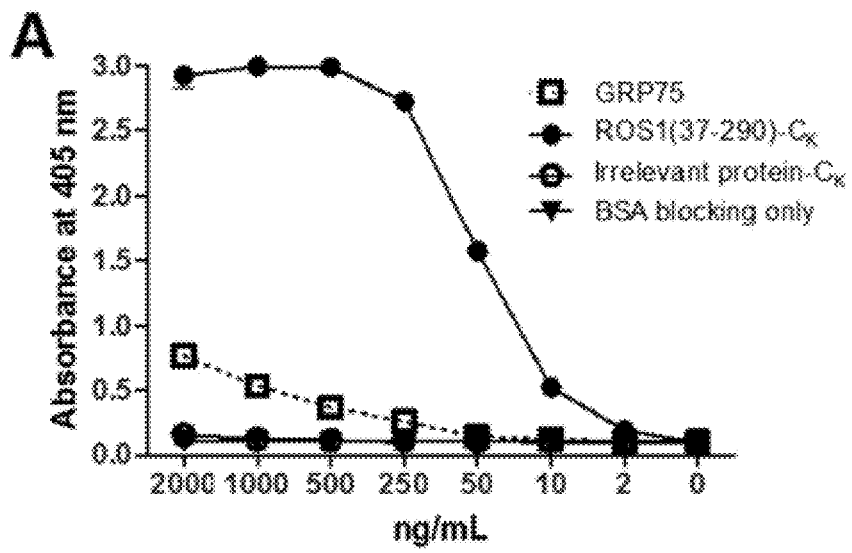
[FIG. 3b]
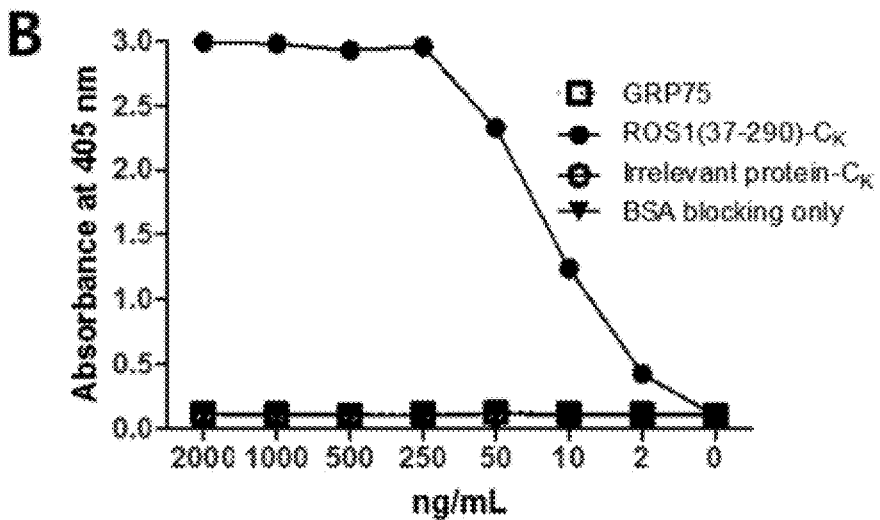

[FIG. 3c]
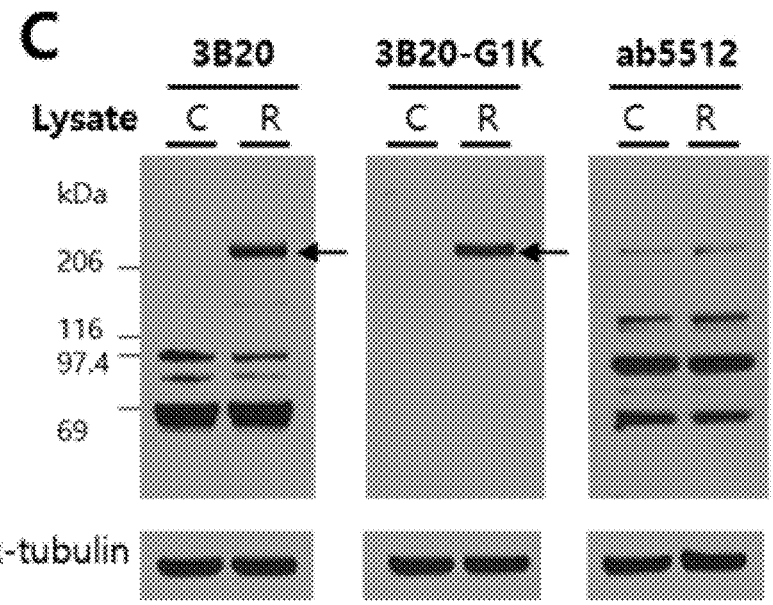
[FIG. 3d]
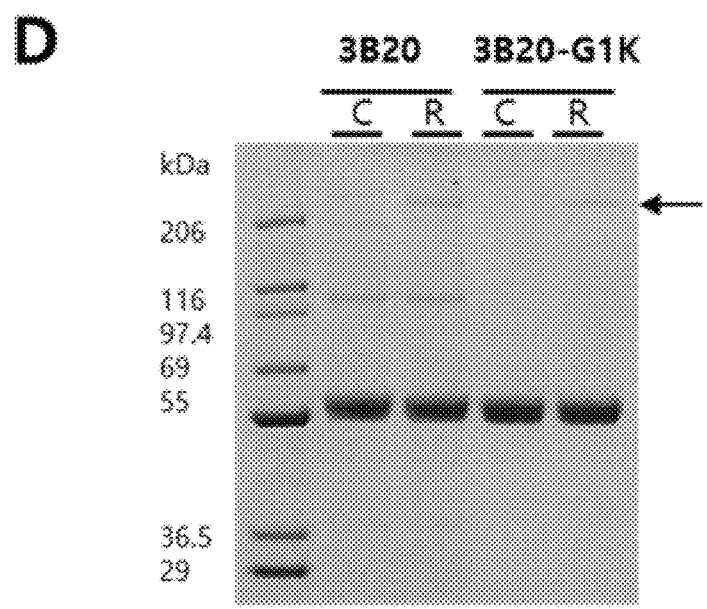

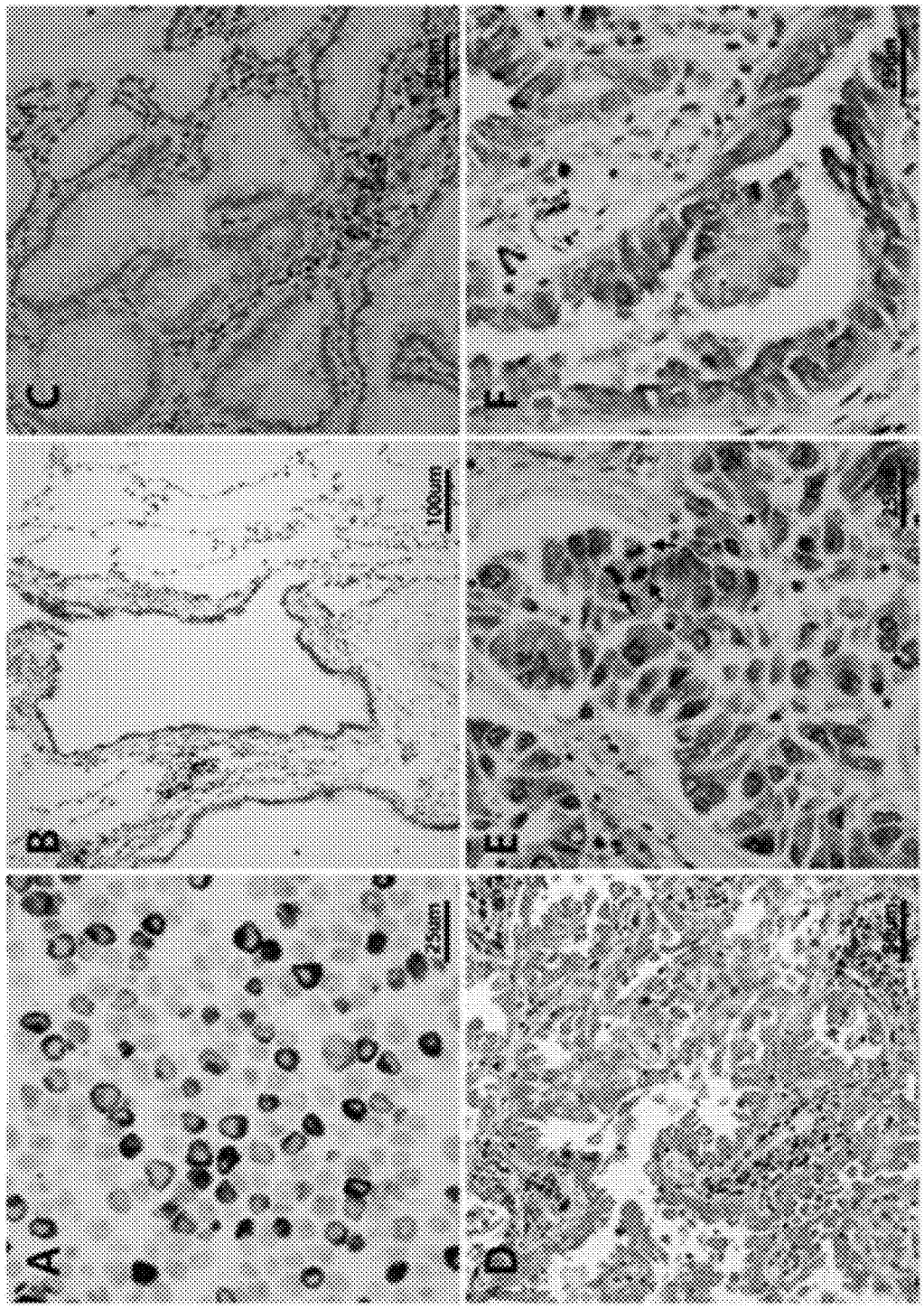
[FIG. 4]

SEQUENCE LISTING

<160> NUMBER OF SEQ ID NOS: 27

<210> SEQ ID NO 1
<211> LENGTH: 8
<212> TYPE: PRT
<213> ORGANISM: Artificial Sequence
<220> FEATURE:
<223> OTHER INFORMATION: Synthetic (LCDR1 of anti-ROS1 antibody)

<400> SEQUENCE: 1

Ser Gly Gly Ser Tyr Gly Tyr Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic (LCDR2 of anti-ROS1 antibody)

<400> SEQUENCE: 2

Asp Asn Thr Asn Arg Pro Ser
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic (LCDR3 of anti-ROS1 antibody)

<400> SEQUENCE: 3

Gly Ser Ala Asp Ser Ser Ser Ile Ala Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic (HCDR1 of anti-ROS1 antibody)

<400> SEQUENCE: 4

Gly Phe Ser Phe Ser Asp Arg Gly Met His
1               5                   10

<210> SEQ ID NO 5
<211> LENGTH: 16
<212> TYPE: PRT
<213> ORGANISM: Artificial Sequence
<220> FEATURE:
<223> OTHER INFORMATION: Synthetic (HCDR2 of anti-ROS1 antibody)

<400> SEQUENCE: 5

Ile Ser Gly Asp Gly Tyr Ile Thr His Tyr Gly Ala Ala Val Lys Gly
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: Synthetic (HCDR3 of anti-ROS1 antibody)

<400> SEQUENCE: 6

Lys Gly Gly Gly Asn Ile Asp Ala
1               5

```
<210> SEQ ID NO 7
<211> LENGTH: 102
<212> TYPE: PRT
<213> ORGANISM: Artificial Sequence
<220> FEATURE:
<223> OTHER INFORMATION: Synthetic (Light chain variable region)

<400> SEQUENCE: 7

Leu Thr Gln Pro Ser Ser Val Ser Ala Asn Leu Gly Gly Thr Val Lys
1               5                   10                  15

Ile Thr Cys Ser Gly Gly Ser Tyr Gly Tyr Gly Trp Tyr Gln Gln Lys
                20                  25                  30

Ala Pro Gly Ser Ala Pro Ala Thr Val Ile Tyr Asp Asn Thr Asn Arg
            35                  40                  45

Pro Ser Asp Ile Pro Ser Arg Phe Ser Gly Ser Lys Ser Gly Ser Thr
    50                  55                  60

Gly Thr Leu Thr Ile Thr Gly Val Gln Val Glu Asp Glu Ala Val Tyr
65                  70                  75                  80

Tyr Cys Gly Ser Ala Asp Ser Ser Ser Ile Ala Thr Phe Gly Ala Gly
                85                  90                  95

Thr Thr Leu Thr Val Leu
            100

<210> SEQ ID NO 8
<211> LENGTH: 119
<212> TYPE: PRT
<213> ORGANISM: Artificial Sequence
<220> FEATURE:
<223> OTHER INFORMATION: Synthetic (Heavy chain variable region)

<400> SEQUENCE: 8

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Ser Phe Ser Asp Arg
                20                  25                  30

Gly Met His Trp Met Arg Gln Ala Pro Gly Lys Gly Leu Glu Tyr Val
            35                  40                  45

Gly Ala Ile Ser Gly Asp Gly Tyr Ile Thr His Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Thr Arg Lys Gly Gly Gly Asn Ile Asp Ala Trp Gly His Gly Thr Glu
            100                 105                 110

Val Ile Val Ser Ser Thr Ser
        115

<210> SEQ ID NO 9
<211> LENGTH: 232
<212> TYPE: PRT
<213> ORGANISM: Artificial Sequence
<220> FEATURE:
<223> OTHER INFORMATION: Synthetic (Human ROS1)

<400> SEQUENCE: 9

Met Lys Asn Ile Tyr Cys Leu Ile Pro Lys Leu Val Asn Phe Ala Thr
1               5                   10                  15
```

-continued

```
Leu Gly Cys Leu Trp Ile Ser Val Val Gln Cys Thr Val Leu Asn Ser
            20                  25                  30

Cys Leu Lys Ser Cys Val Thr Asn Leu Gly Gln Gln Leu Asp Leu Gly
        35                  40                  45

Thr Pro His Asn Leu Ser Glu Pro Cys Ile Gln Gly Cys His Phe Trp
    50                  55                  60

Asn Ser Val Asp Gln Lys Asn Cys Ala Leu Lys Cys Arg Glu Ser Cys
65                  70                  75                  80

Glu Val Gly Cys Ser Ser Ala Glu Gly Ala Tyr Glu Glu Val Leu
                85                  90                  95

Glu Asn Ala Asp Leu Pro Thr Ala Pro Phe Ala Ser Ser Ile Gly Ser
            100                 105                 110

His Asn Met Thr Leu Arg Trp Lys Ser Ala Asn Phe Ser Gly Val Lys
        115                 120                 125

Tyr Ile Ile Gln Trp Lys Tyr Ala Gln Leu Leu Gly Ser Trp Thr Tyr
    130                 135                 140

Thr Lys Thr Val Ser Arg Pro Ser Tyr Val Val Lys Pro Leu His Pro
145                 150                 155                 160

Phe Thr Glu Tyr Ile Phe Arg Val Val Trp Ile Phe Thr Ala Gln Leu
                165                 170                 175

Gln Leu Tyr Ser Pro Pro Ser Pro Ser Tyr Arg Thr His Pro His Gly
            180                 185                 190

Val Pro Glu Thr Ala Pro Leu Ile Arg Asn Ile Glu Ser Ser Ser Pro
        195                 200                 205

Asp Thr Val Glu Val Ser Trp Asp Pro Pro Gln Phe Pro Gly Gly Pro
    210                 215                 220

Ile Leu Gly Tyr Asn Leu Arg Leu
225                 230

<210> SEQ ID NO 10
<211> LENGTH: 4
<212> TYPE: PRT
<213> ORGANISM: Artificial Sequence
<220> FEATURE:
<223> OTHER INFORMATION: Synthetic (Epitope of anti-ROS1 antibody)

<400> SEQUENCE: 10

Asp Leu Gly Thr
1

<210> SEQ ID NO 11
<211> LENGTH: 5
<212> TYPE: PRT
<213> ORGANISM: Artificial Sequence
<220> FEATURE:
<223> OTHER INFORMATION: Synthetic (Epitope of anti-ROS1 antibody)

<400> SEQUENCE: 11

Leu Asp Leu Gly Thr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic (Non-target epitope of anti-ROS1
    antibody)
```

<400> SEQUENCE: 12

Ile Asp Leu Gly Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic (HCDR3 of anti-ROS1 antibody)

<400> SEQUENCE: 13

Gly Gly Gly Gly Asn Ile Asp Ala
1               5

<210> SEQ ID NO 14
<211> LENGTH: 119
<212> TYPE: PRT
<213> ORGANISM: Artificial Sequence
<220> FEATURE:
<223> OTHER INFORMATION: Synthetic (Heavy chain variable region)

<400> SEQUENCE: 14

Ala Val Thr Leu Asp Glu Ser Gly Gly Leu Gln Thr Pro Gly Gly
1               5                   10                  15

Thr Leu Ser Leu Val Cys Lys Ala Ser Gly Phe Ser Phe Ser Asp Arg
            20                  25                  30

Gly Met His Trp Met Arg Gln Ala Pro Gly Lys Gly Leu Glu Tyr Val
        35                  40                  45

Gly Ala Ile Ser Gly Asp Gly Tyr Ile Thr His Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Thr Arg Gly Gly Gly Gly Asn Ile Asp Ala Trp Gly His Gly Thr Glu
            100                 105                 110

Val Ile Val Ser Ser Thr Ser
        115

<210> SEQ ID NO 15
<211> LENGTH: 18
<212> TYPE: PRT
<213> ORGANISM: Artificial Sequence
<220> FEATURE:
<223> OTHER INFORMATION: Synthetic (N-terminal part of Human ROS1)

<400> SEQUENCE: 15

Thr Asn Leu Gly Gln Gln Leu Asp Leu Gly Thr Pro His Asn Leu Ser
1               5                   10                  15

Glu Pro

<210> SEQ ID NO 16
<211> LENGTH: 22
<212> TYPE: PRT
<213> ORGANISM: Artificial Sequence
<220> FEATURE:
<223> OTHER INFORMATION: Synthetic (N-terminal part of Human ROS1 fused
      with GGGC)

<400> SEQUENCE: 16

Thr Asn Leu Gly Gln Gln Leu Asp Leu Gly Thr Pro His Asn Leu Ser
1               5                   10                  15

Glu Pro Gly Gly Gly Cys
            20

<210> SEQ ID NO 17
<211> LENGTH: 40
<212> TYPE: DNA
<213> ORGANISM: Artificial Sequence
<220> FEATURE:
<223> OTHER INFORMATION: Synthetic (Forward primer)
<220> FEATURE:
<221> NAME/KEY: misc_feature
<222> LOCATION: (29)..(31)
<223> OTHER INFORMATION: each n is A, T, G or C

<400> SEQUENCE: 17
ggcccaggcg gcctgtgtaa ctaatctgnn ngaaccgtgt                     40

<210> SEQ ID NO 18
<211> LENGTH: 34
<212> TYPE: DNA
<213> ORGANISM: Artificial Sequence
<220> FEATURE:
<223> OTHER INFORMATION: Synthetic (Reverse primer)

<400> SEQUENCE: 18
ggccggcctg gccttcctct tgttgaactg ctga                          34

<210> SEQ ID NO 19
<211> LENGTH: 24
<212> TYPE: DNA
<213> ORGANISM: Artificial Sequence
<220> FEATURE:
<223> OTHER INFORMATION: Synthetic (Forward primer)

<400> SEQUENCE: 19
ctggctggtt tcgctaccgt ggcc                                     24

<210> SEQ ID NO 20
<211> LENGTH: 21
<212> TYPE: DNA
<213> ORGANISM: Artificial Sequence
<220> FEATURE:
<223> OTHER INFORMATION: Synthetic (Reverse primer)

<400> SEQUENCE: 20
tctggtgcag tagtaggtgg c                                        21

<210> SEQ ID NO 21
<211> LENGTH: 32
<212> TYPE: DNA
<213> ORGANISM: Artificial Sequence
<220> FEATURE:
<223> OTHER INFORMATION: Synthetic (Forward primer)
<220> FEATURE:
<221> NAME/KEY: misc_feature
<222> LOCATION: (21)..(23)
<223> OTHER INFORMATION: each n is A, T, G or C

<400> SEQUENCE: 21
gccaccacta ctgcaccaga nnntggggcc ac                            32

<210> SEQ ID NO 22

```
<211> LENGTH: 24
<212> TYPE: DNA
<213> ORGANISM: Artificial Sequence
<220> FEATURE:
<223> OTHER INFORMATION: Synthetic (Reverse primer)

<400> SEQUENCE: 22
cgggtatgcg ccatggtgat ggtg                                    24

<210> SEQ ID NO 23
<211> LENGTH: 102
<212> TYPE: PRT
<213> ORGANISM: Artificial Sequence
<220> FEATURE:
<223> OTHER INFORMATION: Synthetic (Light chain variable region)

<400> SEQUENCE: 23
```

Leu Thr Gln Pro Ser Ser Val Ser Ala Asn Leu Gly Gly Thr Val Lys
1               5                   10                  15

Ile Thr Cys Ser Gly Gly Ser Tyr Gly Tyr Gly Trp Tyr Gln Gln Lys
            20                  25                  30

Ala Pro Gly Ser Ala Pro Val Thr Val Ile Tyr Asp Asn Thr Asn Arg
        35                  40                  45

Pro Ser Asp Ile Pro Ser Arg Phe Ser Gly Ser Lys Ser Gly Ser Thr
    50                  55                  60

Gly Thr Leu Thr Ile Thr Gly Val Gln Val Glu Asp Glu Ala Val Tyr
65                  70                  75                  80

Tyr Cys Gly Ser Ala Asp Ser Ser Ser Ile Ala Thr Phe Gly Ala Gly
                85                  90                  95

Thr Thr Leu Thr Val Leu
            100

```
<210> SEQ ID NO 24
<211> LENGTH: 239
<212> TYPE: PRT
<213> ORGANISM: Artificial Sequence
<220> FEATURE:
<223> OTHER INFORMATION: Synthetic (anti-ROS1 scFv prolypeptide)

<400> SEQUENCE: 24
```

Leu Thr Gln Pro Ser Ser Val Ser Ala Asn Leu Gly Gly Thr Val Lys
1               5                   10                  15

Ile Thr Cys Ser Gly Gly Ser Tyr Gly Tyr Gly Trp Tyr Gln Gln Lys
            20                  25                  30

Ala Pro Gly Ser Ala Pro Ala Thr Val Ile Tyr Asp Asn Thr Asn Arg
        35                  40                  45

Pro Ser Asp Ile Pro Ser Arg Phe Ser Gly Ser Lys Ser Gly Ser Thr
    50                  55                  60

Gly Thr Leu Thr Ile Thr Gly Val Gln Val Glu Asp Glu Ala Val Tyr
65                  70                  75                  80

Tyr Cys Gly Ser Ala Asp Ser Ser Ser Ile Ala Thr Phe Gly Ala Gly
                85                  90                  95

Thr Thr Leu Thr Val Leu Gly Gln Ser Ser Arg Ser Ser Gly Gly Gly
            100                 105                 110

Gly Ser Ser Gly Gly Gly Ser Ala Val Thr Leu Asp Glu Ser Gly
        115                 120                 125

Gly Gly Leu Gln Thr Pro Gly Thr Leu Ser Leu Val Cys Lys Ala
    130                 135                 140

```
Ser Gly Phe Ser Phe Ser Asp Arg Gly Met His Trp Met Arg Gln Ala
145                 150                 155                 160

Pro Gly Lys Gly Leu Glu Tyr Val Gly Ala Ile Ser Gly Asp Gly Tyr
                165                 170                 175

Ile Thr His Tyr Gly Ala Ala Val Lys Gly Arg Ala Thr Ile Ser Arg
            180                 185                 190

Asp Asn Gly Gln Ser Thr Val Arg Leu Gln Leu Asn Asn Leu Arg Ala
        195                 200                 205

Glu Asp Thr Ala Thr Tyr Tyr Cys Thr Arg Lys Gly Gly Asn Ile
210                 215                 220

Asp Ala Trp Gly His Gly Thr Glu Val Ile Val Ser Ser Thr Ser
225                 230                 235
```

<210> SEQ ID NO 25
<211> LENGTH: 717
<212> TYPE: DNA
<213> ORGANISM: Artificial Sequence
<220> FEATURE:
<223> OTHER INFORMATION: Synthetic (anti-ROS1 scFv gene)

<400> SEQUENCE: 25

```
ctgactcagc cgtcctcggt gtcagcaaac tgggaggaa ccgtcaagat cacctgctcc      60
gggggcagct atggctatgg ctggtaccag cagaaggcac tggcagtgc ccctgccact     120
gtgatctatg acaacaccaa cagaccctcg acatcccctt cacgattctc cggttccaaa     180
tccggctcca cgggcacatt aaccatcact ggggtccaag tcgaggacga ggctgtctat     240
tactgtggga gtcagacag cagcagtatt gctacatttg gggccgggac aaccctgacc     300
gtcctaggtc agtcctctag atcttccggc ggtggtggca gctccggtgg tggcggttcc     360
gccgtgacgt tggacgagtc cggggcggc ctccagacgc ccggaggaac gctcagcctc      420
gtctgcaagg cctccggtt ctccttcagt gaccgtggca tgcactggat gcgacaggct     480
ccaggcaagg ggctggaata cgtcggagct ataagcggtg atggttacat cacacactat     540
ggggcggcgg tgaagggccg tgccaccatc tcgaggaca cgggcagag cacagtgagg     600
ctgcagctga caaacctcag ggctgaggac accgccacct actactgcac cagaaagggt     660
ggtggtaaca tcgacgcatg gggccacggg accgaagtca tcgtctcctc cactagt       717
```

<210> SEQ ID NO 26
<211> LENGTH: 239
<212> TYPE: PRT
<213> ORGANISM: Artificial Sequence
<220> FEATURE:
<223> OTHER INFORMATION: Synthetic (anti-ROS1 scFv polypeptide)

<400> SEQUENCE: 26

```
Leu Thr Gln Pro Ser Ser Val Ser Ala Asn Leu Gly Gly Thr Val Lys
1               5                   10                  15

Ile Thr Cys Ser Gly Gly Ser Tyr Gly Tyr Gly Trp Tyr Gln Gln Lys
            20                  25                  30

Ala Pro Gly Ser Ala Pro Val Thr Val Ile Tyr Asp Asn Thr Asn Arg
        35                  40                  45

Pro Ser Asp Ile Pro Ser Arg Phe Ser Gly Ser Lys Ser Gly Ser Thr
    50                  55                  60

Gly Thr Leu Thr Ile Thr Gly Val Gln Val Glu Asp Glu Ala Val Tyr
65                  70                  75                  80
```

```
Tyr Cys Gly Ser Ala Asp Ser Ser Ile Ala Thr Phe Gly Ala Gly
                85                  90                  95

Thr Thr Leu Thr Val Leu Gly Gln Ser Ser Arg Ser Ser Gly Gly
           100                 105                 110

Gly Ser Ser Gly Gly Gly Ser Ala Val Thr Leu Asp Glu Ser Gly
        115                 120                 125

Gly Gly Leu Gln Thr Pro Gly Gly Thr Leu Ser Leu Val Cys Lys Ala
    130                 135                 140

Ser Gly Phe Ser Phe Ser Asp Arg Gly Met His Trp Met Arg Gln Ala
145                 150                 155                 160

Pro Gly Lys Gly Leu Glu Tyr Val Gly Ala Ile Ser Gly Asp Gly Tyr
                165                 170                 175

Ile Thr His Tyr Gly Ala Ala Val Lys Gly Arg Ala Thr Ile Ser Arg
            180                 185                 190

Asp Asn Gly Gln Ser Thr Val Arg Leu Gln Leu Asn Asn Leu Arg Ala
        195                 200                 205

Glu Asp Thr Ala Thr Tyr Tyr Cys Thr Arg Gly Gly Gly Asn Ile
    210                 215                 220

Asp Ala Trp Gly His Gly Thr Glu Val Ile Val Ser Ser Thr Ser
225                 230                 235
```

<210> SEQ ID NO 27
<211> LENGTH: 717
<212> TYPE: DNA
<213> ORGANISM: Artificial Sequence
<220> FEATURE:
<223> OTHER INFORMATION: Synthetic (anti-ROS1 scFv gene)

<400> SEQUENCE: 27

```
ctgactcagc cgtcctcggt gtcagcaaac ctgggaggaa ccgtcaagat cacctgctcc      60
gggggcagct atggctatgg ctggtaccag cagaaggcac ctgcagtgc cctgtcact      120
gtgatctatg acaacaccaa cagaccctcg gacatccctt cacgattctc cggttccaaa    180
tccggctcca cgggcacatt aaccatcact ggggtccaag tcgaggacga ggctgtctat    240
tactgtggga gtgcagacag cagcagtatt gctacatttg ggccgggac aaccctgacc    300
gtcctaggtc agtcctctag atcttccggc ggtggtggca gctccggtgg tggcggttcc    360
gccgtgacgt tggacgagtc cggggcggc ctccagacgc ccgaggaaac gctcagcctc    420
gtctgcaagg cctccgggtt ctccttcagt gaccgtggca tgcactggat gcgacaggct    480
ccaggcaagg gctggaata cgtcggagct ataagcggtg atggttacat cacacactat    540
ggggcggcgg tgaagggccg tgccaccatc tcgagggaca cgggcagag cacagtgagg    600
ctgcagctga acaacctcag ggctgaggac accgccacct actactgcac cagaggtggt    660
ggtggtaaca tcgacgcatg gggccacggg accgaagtca tcgtctcctc cactagt      717
```

ANTI-ROS1 ANTIBODY AND USE THEREOF

TECHNICAL FIELD

Provided is an anti-ROS1 antibody with improved specificity to ROS1 and uses thereof, and specifically, an anti-ROS1 antibody or antigen-binding fragment thereof, and a use thereof in cancer diagnosis.

BACKGROUND ART

Traditionally, monoclonal antibodies (hybrid monoclonal antibodies, mAbs) have been generated using hybridoma technologies and their identities have been defined by hybridoma cell lines deposited in public cell line banks.

The development of recombinant antibody technology allows the generation of monoclonal antibodies and determination of their sequence at the same time. This has enabled the development of daughter antibodies from the initial mAb clone by introducing mutations, which enable higher affinity and better physicochemical properties.

However, there are few reports on whether the specificity of mAbs can be enhanced in the same way. In fact, more than 50% of commercially available antibodies have poor specificity or do not work at all. In addition, antibodies may have cross-reactivity with nonspecific targets.

Here, we selected the proto-oncogene tyrosine kinase ROS1 (ROS1) as a target antigen, being one of the orphan receptor tyrosine kinases. It was first reported and isolated from human glioblastoma cells. The ROS1 gene on chromosome 6922 is subject to rearrangement with various partners. Therefore, the protein is truncated and expressed in fusion forms in which the 30 regions of ROS1 is fused to the 50 regions of v-ros, FIG, SLC34A2, CD74, EZR, LRIG3, and TPM3 in various cancers including non-small cell lung cancers and human cholangiocarcinomas. ROS1 is known to activate cell signaling associated with proliferation, metastasis, and anti-apoptotic functions; however, its biological functions remain unclear.

Accordingly, the development of an antibody against ROS1 with enhanced specificity to a target antigen, which has a high affinity with the target antigen and has no affinity for a non-target protein, and a technology for diagnosis of various cancers using the same.

DISCLOSURE

Technical Problem

In this disclosure, provided are an epitope of ROS1 which can improve specificity to ROS1, an anti-ROS1 antibody or antigen-binding fragment thereof which specifically recognizes the epitope, and a use of the antibody. The anti-ROS1 antibody or antigen-binding fragment may recognize a specific region of ROS1, thereby having a characteristic of more enhanced specificity to ROS1.

One embodiment provides an anti-ROS1 antibody or antigen-binding fragment thereof specifically recognizing the N-terminal region of ROS1 protein.

ROS1 protein may be human ROS1 (for example, NP_002935.2 (SEQ ID NO: 9), etc.). The N-terminal region of ROS1 protein may be the $37^{th}$ to $290^{th}$ region of the amino acid sequence of ROS1 protein (SEQ ID NO: 9) or part thereof, and the part may be the $39^{th}$ to $56^{th}$ region of ROS1 protein (SEQ ID NO: 9), or part thereof (for example, an amino acid of D46-L47-G48-T49 (SEQ ID NO: 10) or L45-D46-L47-G48-T49 (SEQ ID NO: 11)).

In an embodiment, the anti-ROS1 antibody or antigen-binding fragment thereof may specifically recognize amino acids 39-56 of ROS1 (NP_002935.2; SEQ ID NO: 9) or part thereof (for example, an amino acid of D46-L47-G48-T49 (SEQ ID NO: 10) or L45-D46-L47-G48-T49 (SEQ ID NO: 11) of ROS1).

For example, the anti-ROS1 antibody or antibody-derived antigen-binding fragment may comprise D46-L47-G48-T49 (SEQ ID NO: 10) or L45-D46-L47-G48-T49 (SEQ ID NO: 11) of ROS1, or specifically recognize (and/or bind to) an epitope consisting of these amino acids essentially.

In another embodiment, the anti-ROS1 antibody or antigen-binding fragment thereof provided herein may not bind to the peptide composed of IDLGT (SEQ ID NO: 12). The peptide composed of IDLGT may be present in HSP-based protein such as Heat shock protein 70 (HSP70), HSP71, GRP75 and GRP78, and the like. Therefore, the anti-ROS1 antibody or antigen-binding fragment thereof provided herein may not bind to the HSP-based protein such as HSP70, HSP71, GRP75 and GRP78, and the like.

The anti-ROS1 antibody or antigen-binding fragment thereof may comprise the following complementarity determining regions:

```
LCDR1:
                                    (SEQ ID NO: 1)
SGGSYGYG,

LCDR2:
                                    (SEQ ID NO: 2)
DNTNRPS,

LCDR3:
                                    (SEQ ID NO: 3)
GSADSSSIAT,

HCDR1:
                                    (SEQ ID NO: 4)
GFSFSDRGMH,

HCDR2:
                                    (SEQ ID NO: 5)
ISGDGYITHYGAAVKG,
and

HCDR3:
XGGGNIDA (X is K or G).
```

The HCDR3 may be SEQ ID NO: 6 (KGGGNIDA) or SEQ ID NO: 13 (GGGGNIDA), and particularly, it may be SEQ ID NO: 6 (KGGGNIDA).

The anti-ROS1 antibody or antigen-binding fragment thereof may comprise the following variable regions:

```
light chain variable region:
                                    (SEQ ID NO: 7)
LTQPSSVSANLGGTVKITC SGGSYGYG
WYQQKAPGSAPATVIY DNTNRPS DIPSRFSGSKSGSTGTLTITGVQVEDEAVYYC
GSADSSSIAT FGAGTTLTVL,
or
```

-continued light chain variable region:
(SEQ ID NO: 23)
LTQPSSVSANLGGTVKITC
SGGSYGYG WYQQKAPGSAPVTVIY DNTNRPS
DIPSRFSGSKSGSTGTLTITGVQVEDEAVYYC GSADSSSIAT FGAGTTLTVL;
and heavy chain variable region:
(SEQ ID NO: 8)
AVTLDESGGGLQTPGGTLSLVCKAS
GFSFSDRGMH WMRQAPGKGLEYVGA ISGDGYITHYGAAVKG
RATISRDNGQSTVRLQLNNLRAEDTATYYCTR KGGGNIDA WGHGTEVIVSSTS,
or (SEQ ID NO: 14)
AVTLDESGGGLQTPGGTLSLVCKAS GFSFSDRGMH
WMRQAPGKGLEYVGA ISGDGYITHYGAAVKG
RATISRDNGQSTVRLQLNNLRAEDTATYYCTR GGGGNIDA WGHGTEVIVSSTS (Among the amino acid sequences of the variable regions, LCDR1, LCDR2, LCDR3, HCDR1, HCDR2, and HCDR3 are underlined in order).

Another embodiment provides a pharmaceutical composition comprising the anti-ROS1 antibody or antigen-binding fragment thereof. For example, the pharmaceutical composition may be a composition for cancer diagnosis.

Another embodiment provides a use for use in cancer diagnosis, or a use for use in manufacture of an anti-cancer agent or cancer diagnostic agent, of the anti-ROS1 antibody or antigen-binding fragment thereof.

Another embodiment provides a method for diagnosing cancer or providing information for diagnosis of cancer, comprising
  (1) contacting (reacting) the anti-ROS1 antibody or antigen-binding fragment to a biological sample isolated from a subject; and
  (2) confirming an antigen-antibody reaction or antigen-antibody complex formation between the antibody or antigen-binding fragment and antigen (ROS1 protein) in the reactant of the step (1).

The method for diagnosing cancer or providing information for diagnosis of cancer may further comprise
  (3) determining (or confirming) that the subject has cancer or is at risk of developing cancer, when the antigen-antibody reaction is confirmed or the formation of the antigen-antibody complex is confirmed (the complex is detected) in the reactant of the step (1), after the confirming step (2).

Another embodiment provides an epitope of ROS1 which can improve specificity to ROS1 of the anti-ROS1 antibody. The epitope may be the N-terminal region of ROS1 protein (for example, the 37$^{th}$ to 290$^{th}$ region of the amino acid sequence of GenBank Accession No. NP_002935.2 (SEQ ID NO: 9)) or part thereof (for example, a region comprising consecutive 4 or more or 5 or more (for example, 4, 5, 6, 7, 8, 9 or 10) amino acids in the N-terminal region or consisting of the same). In one embodiment, the epitope of ROS1 may be the 39$^{th}$ to 56$^{th}$ region of ROS1 protein (SEQ ID NO: 9), or part thereof (for example, an amino acid of D46-L47-G48-T49 (SEQ ID NO: 10) or L45-D46-L47-G48-T49 (SEQ ID NO: 11)).

Another embodiment provides a method for manufacturing an antibody or antigen-binding fragment specifically binding to ROS1 comprising
  contacting a candidate antibody or antigen-binding fragment to the epitope of ROS1; and
  selecting the antibody or antigen-binding fragment binding to the epitope of ROS1.

One embodiment provides a method for improving specificity of an anti-ROS1 antibody, comprising introducing point mutation into a heavy chain complementarity determining region 3 (HCDR3). In one embodiment, the method for improving specificity of an anti-ROS1 antibody may comprise substituting glycine (G) which is the first amino acid of HCDR3 of the antibody or antigen-binding fragment thereof comprising the following CDRs to lysine (K):

LCDR1:
(SEQ ID NO: 1)
SGGSYGYG,

LCDR2:
(SEQ ID NO: 2)
DNTNRPS,

LCDR3:
(SEQ ID NO: 3)
GSADSSSIAT,

HCDR1:
(SEQ ID NO: 4)
GFSFSDRGMH,

HCDR2:
(SEQ ID NO: 5)
ISGDGYITHYGAAVKG,
and

HCDR3:
(SEQ ID NO: 13)
GGGGNIDA.

Another embodiment provides a nucleic acid molecule encoding a polypeptide selected from the group consisting of CDR (LCDR1 (SEQ ID NO: 1), LCDR2 (SEQ ID NO: 2), LCDR3 (SEQ ID NO: 3), HCDR1 (SEQ ID NO: 4), HCDR2 (SEQ ID NO: 5), and HCDR3 (SEQ ID NO: 6)), light chain variable region (SEQ ID NO: 7 or SEQ ID NO: 23), heavy chain variable region (SEQ ID NO: 8 or SEQ ID NO: 13), and scFv (SEQ ID NO: 24 or SEQ ID NO: 26) of the anti-ROS1 antibody.

Another embodiment provides a recombinant vector comprising the nucleic acid molecule. In one embodiment, the recombinant vector may comprise the light chain variable region (SEQ ID NO: 7) and the heavy chain variable region (SEQ ID NO: 8 or SEQ ID NO: 14), respectively or together. In other embodiment, the recombinant vector may comprise the anti-ROS1 scFv (SEQ ID NO: 24 or SEQ ID NO: 26).

Another embodiment provides a recombinant cell comprising the recombinant vector.

Another embodiment provides a manufacturing method of an anti-ROS1 antibody or antigen-binding fragment thereof comprising expressing the recombinant cell.

Technical Solution

The proto-oncogene tyrosine kinase ROS1 plays a key role in carcinogenesis through gene rearrangement to form a fusion protein with other genes, in which the C-terminal intracellular region of ROS1 participates. The possibility of wild type ROS1 overexpression through epigenetic regulation has been proposed. In one embodiment, an anti-ROS1 antibody binding to the N-terminal of ROS1 (3B20) is provided, and this can be used for the detection of wild type ROS1 in cancer tissues (for example, cancerous tissues). In one embodiment, using common analysis technology such as immunoblot and immunoprecipitation analyses, it was found that 3B20 also reacted with heat shock proteins (for example, Hsp70s). By analyzing the amino acid sequence of ROS1 and the amino acid sequence of Hsp70s, it was found that these sequences share an identical amino acid sequence, DLGT. Through the test of alanine mutagenesis of ROS1, the epitope was found to harbor this sequence. In other embodiment, through random mutation which substitutes each amino acid composing HCDR3 of the anti-ROS1 antibody (3B20) to other amino acid different from the original amino acid, a mutant clone 3B20-G1K which maintains the reactivity (binding ability) to ROS1 and has no cross-reactivity reacting with other proteins (for example, Hsp70s, etc.) was produced. In other embodiment, using 3B20-G1K, it was confirmed that while ROS1 was not observed in the normal tissue (for example, normal lung tissue), ROS1 was overexpressed in the lung cancer tissue (for example, lung tissue having lung adenocarcinoma).

Based on this matter, herein, provided are an epitope of ROS1 which can improve specificity to ROS1, an anti-ROS1 antibody specifically recognizing the epitope or antigen-binding fragment thereof, and a use of the antibody. The anti-ROS1 antibody or antigen-binding fragment thereof may recognize a certain region of ROS1, thereby having a characteristic of enhanced specificity to ROS1.

One embodiment provides an anti-ROS1 antibody specifically recognizing the N-terminal region of ROS1 protein or antigen-binding fragment thereof.

ROS1 protein may be human ROS1 (for example, NP_002935.2 (SEQ ID NO: 9), etc.). The N-terminal region of ROS1 protein may be the 37$^{th}$ to 290$^{th}$ regions of the amino acid sequence of ROS1 protein (SEQ ID NO: 9) or part thereof, and the part may be for example, the 39$^{th}$ to 56$^{th}$ regions of ROS1 protein (SEQ ID NO: 9), or part thereof (for example, an amino acid of D46-L47-G48-T49 (SEQ ID NO: 10) or L45-D46-L47-G48-T49 (SEQ ID NO: 11)).

In one embodiment, the anti-ROS1 antibody or antigen-binding fragment thereof may specifically recognize the amino acids 39-56 of ROS1 (NP_002935.2; SEQ ID NO: 9) or part thereof (for example, an amino acid of D46-L47-G48-T49 (SEQ ID NO: 10) or L45-D46-L47-G48-T49 (SEQ ID NO: 11) of ROS1).

For example, the anti-ROS1 antibody or antigen-binding fragment thereof may specifically recognize an epitope which comprises D46-L47-G48-T49 (SEQ ID NO: 10) or L45-D46-L47-G48-T49 (SEQ ID NO: 11) of ROS1 or consists of these amino acids essentially.

In one embodiment, the anti-ROS1 antibody or antigen-binding fragment thereof may not bind (and/or recognize) to the peptide consisting of IDLGT (SEQ ID NO: 12). The peptide consisting of IDLGT may be present in HSP-based proteins such as Heat shock protein 70 (HSP70), HSP71, GRP75 and GRP78, and the like. Accordingly, the anti-ROS1 antibody or antigen-binding fragment thereof provided herein may bot bind to HSP-based proteins such as HSP70, HSP71, GRP75 and GRP78, and the like.

In other embodiment, the anti-ROS1 antibody or antigen-binding fragment thereof may bind (and/or recognize) to the peptide consisting of L45-D46-L47-G48-T49 (SEQ ID NO: 11) and IDLGT (SEQ ID NO: 12). In this case, the anti-ROS1 antibody or antigen-binding fragment thereof may bind (and/or recognize) to all of one or more kinds, 2 or more kinds, 3 or more kinds, 4 or more kinds, or 5 or more kinds selected from the group consisting of ROS1 and HSP-based proteins such as HSP70, HSP71, GRP75 and GRP78, and the like.

The anti-ROS1 antibody or antigen-binding fragment thereof may comprise the following complementarity determining regions (CDRs):

```
LCDR1:
                                       (SEQ ID NO: 1)
SGGSYGYG,

LCDR2:
                                       (SEQ ID NO: 2)
DNTNRPS,

LCDR3:
                                       (SEQ ID NO: 3)
GSADSSSIAT,

HCDR1:
                                       (SEQ ID NO: 4)
GFSFSDRGMH,

HCDR2:
                                       (SEQ ID NO: 5)
ISGDGYITHYGAAVKG,
and HCDR3:
XGGGNIDA (X is K or G).
```

The HCDR3 may be SEQ ID NO: 6 (KGGGNIDA) or SEQ ID NO: 13 (GGGGNIDA), and in particular, it may be SEQ ID NO: 6 (KGGGNIDA).

The anti-ROS1 antibody or antigen-binding fragment thereof may comprise the following variable regions:

```
light chain variable region:
                                                    (SEQ ID NO: 7)
LTQPSSVSANLGGTVKITC SGGSYGYG
WYQQKAPGSAPATVIY DNTNRPS DIPSRFSGSKSGSTGTLTITGVQVEDEAVYYC
GSADSSSIAT FGAGTTLTVL,
or (SEQ ID NO: 23)
LTQPSSVSANLGGTVKITC
SGGSYGYG WYQQKAPGSAPVTVIY DNTNRPS
DIPSRFSGSKSGSTGTLTITGVQVEDEAVYYC GSADSSSIAT FGAGTTLTVL;
and
```

```
heavy chain variable region:
                                                        (SEQ ID NO: 8)
AVTLDESGGGLQTPGGTLSLVCKAS
GFSFSDRGMH WMRQAPGKGLEYVGA ISGDGYITHYGAAVKG
RATISRDNGQSTVRLQLNNLRAEDTATYYCTR KGGGNIDA WGHGTEVIVSSTS,
or
                                                        (SEQ ID NO: 14)
AVTLDESGGGLQTPGGTLSLVCKAS GFSFSDRGMH
WMRQAPGKGLEYVGA ISGDGYITHYGAAVKG
RATISRDNGQSTVRLQLNNLRAEDTATYYCTR GGGGNIDA WGHGTEVIVSSTS
```

(In the amino acid sequence of the variable regions, LCDR1, LCDR2, LCDR3, HCDR1, HCDR2, and HCDR3 are underlined in order).

In one embodiment, the anti-ROS1 antibody or antigen-binding fragment thereof may be an anti-ROS1 antibody or antigen-binding fragment thereof defined as follows:

(1) an anti-ROS1 antibody or antigen-binding fragment thereof comprising the following complementarity determining regions (CDRs):
LCDR1 comprising the amino acid sequence of SEQ ID NO: 1 (SGGSYGYG),
LCDR2 comprising the amino acid sequence of SEQ ID NO: 2 (DNTNRPS),
LCDR3 comprising the amino acid sequence of SEQ ID NO: 3 (GSADSSSIAT).
HCDR1 comprising the amino acid sequence of SEQ ID NO: 4 (GFSFSDRGMH),
HCDR2 comprising the amino acid sequence of SEQ ID NO: 5 (ISGDGYITHYGAAVKG), and
HCDR3 comprising the amino acid sequence of SEQ ID NO: 6 (KGGGNIDA); or (2) an anti-ROS1 antibody or antigen-binding fragment thereof comprising the following variable regions:
a light chain variable region comprising the amino acid sequence of SEQ ID NO: 7; and
a heavy chain variable region comprising the amino acid sequence of SEQ ID NO: 8,
and in this case, the anti-ROS1 antibody or antigen-binding fragment thereof may bind to SEQ ID NO: 11 (LDLGT) and not bind to SEQ ID NO: 12 (IDLGT), and due to this characteristic, it may specifically bind to ROS1 protein.

In other embodiment, the anti-ROS1 antibody or antigen-binding fragment thereof may be an anti-ROS1 antibody or antigen-binding fragment thereof defined as follows:

(1) an anti-ROS1 antibody or antigen-binding fragment thereof comprising the following complementarity determining regions (CDRs):
LCDR1 comprising the amino acid sequence of SEQ ID NO: 1 (SGGSYGYG),
LCDR2 comprising the amino acid sequence of SEQ ID NO: 2 (DNTNRPS),
LCDR3 comprising the amino acid sequence of SEQ ID NO: 3 (GSADSSSIAT).
HCDR1 comprising the amino acid sequence of SEQ ID NO: 4 (GFSFSDRGMH),
HCDR2 comprising the amino acid sequence of SEQ ID NO: 5 (ISGDGYITHYGAAVKG), and
HCDR3 comprising the amino acid sequence of SEQ ID NO: 13 (GGGGNIDA); or (2) an anti-ROS1 antibody or antigen-binding fragment thereof comprising the following variable regions:
a light chain variable region comprising the amino acid sequence of SEQ ID NO: 23; and
a heavy chain variable region comprising the amino acid sequence of SEQ ID NO: 14,
and in this case, the anti-ROS1 antibody or antigen-binding fragment thereof may bind to SEQ ID NO: 11 (LDLGT) and SEQ ID NO: 12 (IDLGT), and due to this characteristic, it may bind to all of one or more kinds, 2 or more kinds, 3 or more kinds, 4 or more kinds, or 5 or more kinds selected from the group consisting of ROS1, Hsp70, Hsp71, GRP75, and GRP78.

As described herein, the antigen-binding fragment of the anti-ROS1 antibody may be any polypeptide comprising 6 CDRs of the anti-ROS1 antibody, for example, scFv, scFv-Fc, scFv-Cκ (kappa invariable region), scFv-Cλ (lambda invariable region), (scFv)$_2$, Fab, Fab' or F(ab')$_2$, but not limited thereto. In one embodiment, the antigen-binding fragment may be scFv, or a fusion polypeptide in which scFv is fused with Fc region of an immunoglobulin (for example, IgG1, IgG2, IgG3, IgG4, etc.) (scFv-Fc) or a fusion polypeptide fused with a light chain invariable region (for example, kappa or lambda) (scFv-Cκ or scFv-Cλ).

The anti-ROS1 antibody or antigen-binding fragment thereof may specifically recognize and bind to the N-terminal region not the C-terminal of ROS1 protein which plays an important role in carcinogenesis in ROS1 protein. Therefore, ROS1 protein involved in carcinogenesis may be detected using the anti-ROS1 antibody or antigen-binding fragment thereof, and through this, it may be used for diagnosis of diseases (for example, cancer, etc.) related to expression (presence) or overexpression of ROS1.

Accordingly, herein, a pharmaceutical composition comprising the anti-ROS1 antibody or antigen-binding fragment thereof is provided. For example, the pharmaceutical composition may be a composition for cancer diagnosis.

Another embodiment, a use for use in diagnosis of cancer or a use for use in preparation of an anti-cancer agent or a cancer diagnosing agent, of the anti-ROS1 antibody or antigen-binding fragment thereof is provided.

Another embodiment provides a method for cancer diagnosis or a method for providing information for cancer diagnosis, comprising:
(1) contacting (reacting) the anti-ROS1 antibody or antigen-binding fragment thereof to a biological sample isolated from a subject (patient); and
(2) confirming an antigen-antibody reaction between the antibody or antigen-binding fragment and an antigen (ROS1 protein) in the reactant of the step (1).

The step of confirming the antigen-antibody reaction may be performed by a step of confirming formation of an antigen-antibody complex (detecting a complex) by a common method. The biological sample may be selected from the group consisting of a cell, tissue, body fluid, culture thereof, and the like, obtained (isolated) form the subject (for example, mammals such as human, etc.).

The method for cancer diagnosis or method for providing information for cancer diagnosis may further comprise:

(3) determining (or confirming) that the subject has cancer or is at risk of developing cancer, when the antigen-antibody reaction is confirmed or the formation of the antigen-antibody complex is confirmed (the complex is detected) in the reactant of the step (1), after the confirming step (2).

Another embodiment provides an epitope of ROS1 which can improve specificity to ROS1 of the anti-ROS1 antibody. The epitope may be the N-terminal region of ROS1 protein (for example, the 37$^{th}$ to 290$^{th}$ region of the amino acid sequence of GenBank Accession No. NP_002935.2 (SEQ ID NO: 9)) or part thereof (for example, a region comprising consecutive 4 or more or 5 or more amino acids in the N-terminal region or consisting of the same). In one embodiment, the epitope of ROS1 may be the 39$^{th}$ to 56$^{th}$ region (SEQ ID NO: 15) of ROS1 protein (SEQ ID NO: 9), or part thereof (for example, an amino acid comprising D46-L47-G48-T49 (SEQ ID NO: 10) or L45-D46-L47-G48-T49 (SEQ ID NO: 11), or a region comprising 4 or more or 5 or more consecutive amino acids comprising SEQ ID NO: 10 or SEQ ID NO: 11 in SEQ ID NO: 9 or consisting of the same).

Another embodiment provides a method for manufacturing an antibody or antigen-binding fragment specifically binding to ROS1 comprising contacting a candidate antibody or antigen-binding fragment to the N-terminal region of ROS1 (for example, aforementioned epitope); and selecting the antibody or antigen-binding fragment binding to the epitope of ROS1. In one embodiment, when the epitope is SEQ ID NO: 10 (DLGT), the selected antibody or antigen-binding fragment may bind to SEQ ID NO: 11 (IDLGT) and SEQ ID NO: 12 (IDLGT), and it may bind to all of one or more kinds, 2 or more kinds, 3 or more kinds, 4 or more kinds or 5 or more kinds selected from the group consisting of ROS1, Hsp70, Hsp71, GRP75, and GRP78. In other embodiment, when the epitope is SEQ ID NO: 11 (IDLGT), the selected antibody or antigen-binding fragment may bind to SEQ ID NO: 11 (IDLGT), but not bind to SEQ ID NO: 12 (IDLGT), and specifically bind to ROS1.

In one embodiment, a method for enhancing specificity of an anti-ROS1 antibody, comprising introducing point mutation to a heavy chain complementarity determining region 3 (HCDR3) is provided. In one embodiment, the method for enhancing the specificity of the anti-ROS1 antibody may comprise substituting the first amino acid of the HCDR3 of the antibody or antigen-binding fragment comprising the following CDRs to lysine (K):

```
LCDR1:
                                    (SEQ ID NO: 1)
SGGSYGYG,

LCDR2:
                                    (SEQ ID NO: 2)
DNTNRPS,

LCDR3:
                                    (SEQ ID NO: 3)
GSADSSSIAT,

HCDR1:
                                    (SEQ ID NO: 4)
GFSFSDRGMH,
```

```
-continued
HCDR2:
                                    (SEQ ID NO: 5)
ISGDGYITHYGAAVKG,
and

HCDR3:
                                    (SEQ ID NO: 13)
GGGGNIDA.
```

Another embodiment provides a nucleic acid molecule encoding a polypeptide selected from the group consisting of CDR (LCDR1 (SEQ ID NO: 1), LCDR2 (SEQ ID NO: 2), LCDR3 (SEQ ID NO: 3), HCDR1 (SEQ ID NO: 4), HCDR2 (SEQ ID NO: 5), and HCDR3 (SEQ ID NO: 6), a light chain variable region (SEQ ID NO: 7 or SEQ ID NO: 23), a heavy chain variable region (SEQ ID NO: 8 or SEQ ID NO: 13), and scFv (SEQ ID NO: 24 or SEQ ID NO: 26) of the anti-ROS1 antibody.

Another embodiment provides a recombinant vector comprising the nucleic acid molecule. In one embodiment, the recombinant vector may comprise each of the light chain variable region (SEQ ID NO: 7) and the heavy chain variable region (SEQ ID NO: 8 or SEQ ID NO: 14) or together. In other embodiment, the recombinant vector may comprise the anti-ROS1 scFv (SEQ ID NO: 24 or SEQ ID NO: 26).

Another embodiment provides a recombinant cell comprising the recombinant vector.

Another embodiment provides a manufacturing method of an anti-ROS1 antibody or antigen-binding fragment thereof comprising expressing the recombinant cell.

ROS1 acting as an antigen of the antibody or antigen-binding fragment provided herein may be derived from a mammal, and for example, it may be human-derived ROS1 (for example, GenBank accession numbers NP_002935.2, etc.). The anti-ROS1 antibody provided herein recognizes and/or binds to the N-terminal region of ROS1 (i.e., the aforementioned epitope region).

Herein, "antibody" refers to a protein specifically binding to a specific antigen, and it may be a protein made by stimuli of an antigen in the immune system or a protein chemically synthesized or recombinantly manufactured from it, and its kind is not particularly limited. The antibody may be non-naturally produced, for example, recombinantly or synthetically produced. The antibody may be an animal antibody (for example, a mouse antibody, etc.), a chimeric antibody, a humanized antibody or a human antibody. The antibody may be a monoclonal antibody or polyclonal antibody.

A complete antibody has a structure having 2 full length light chains and 2 full length heavy chains, and each light chain is connected to a heavy chain by disulfide bond. An invariable region of the antibody is divided into a heavy chain invariable region and a light chain invariable region, and the heavy chain invariable region has gamma (γ), mu (μ), alpha (α), delta (δ) and epsilon (ε) types, and has gamma1 (γ1), gamma2 (γ2), gamma3 (γ3), gamma4 (γ4), alpha1 (α1) and alpha2 (α2) as subclasses. The invariable region of the light chain has kappa (κ) and lambda (λ) types.

The term, "heavy chain" is interpreted as including all of the full-length heavy chain comprising a variable region domain $V_H$ comprising an amino acid sequence having a sufficient variable region sequence to provide specificity to an antigen and 3 invariable region domains, $C_{H1}$, $C_{H2}$ and $C_{H3}$ and hinge, and fragment thereof. In addition, the term, "light chain" is interpreted as including all of the full-length light chain comprising a variable region domain $V_L$ comprising an amino acid sequence having a sufficient variable region sequence to provide specificity to an antigen, and an invariable region domain $C_L$, and fragment thereof.

The term, "CDR (complementarity determining region)" means a region providing binding specificity to an antigen in a variable region of an antibody, and means an amino acid sequence of a hypervariable region of a heavy chain and a light chain of an immunoglobulin. The heavy chain and light chain may comprise 3 CDRs (CDRH1, CDRH2, CDRH3 and CDRL1, CDRL2, CDRL3), respectively. The CDR may provide a major contact residue in binding of an antibody to an antigen or epitope. On the other hand, herein, the term, "specifically binding" or "specifically recognizing" is the same meaning as commonly known to those skilled in the art, and means that an antigen and an antibody interact specifically and react immunologically.

Herein, the antibody may be understood by comprising an antigen-binding fragment of the antibody which retains antigen-binding ability, unless otherwise mentioned.

The term, "antigen-binding fragment" means all types of polypeptides comprising a part where an antigen can bind (for example, 6 CDRs defined herein). For example, it may be scFv, (scFv)$_2$, Fab, Fab' or F(ab')$_2$ of an antibody, but not limited thereto. In addition, as aforementioned, the antigen-binding fragment may be scFv, or a fusion polypeptide in which scFv is fused with Fc region of an immunoglobulin (for example, IgG1, IgG2, IgG3, IgG4, etc.) or an invariable region of a light chain (for example, kappa or lambda).

Fab of the antigen-binding fragment has a structure having a variable region of a light chain and a heavy chain and an invariable region of a light chain and the first invariable region of a heavy chain ($C_{H1}$), and has one antigen-binding region.

Fab' is different from Fab in that it has a hinge region comprising one or more of cysteine residues at the C-terminal of the heavy $C_{H1}$ domain.

F(ab')$_2$ antibody is produced by disulfide bond of the cysteine residue of the hinge region. Fv is a minimal antibody fragment having only a heavy chain variable region and a light chain variable region, and the recombination technology producing an Fv fragment is widely known in the art.

Two-chain Fv has a heavy chain variable region and a light chain variable region connected by non-covalent bond, and single-chain Fv generally has a heavy chain variable region and a light chain variable region connected by covalent bond or connected at the C-terminal directly, and therefore it may achieve a dimer-like structure like the two-chain Fv.

The antigen-binding fragment may be obtained using a protease (for example, restriction cutting of the total antibody with papain yields Fab and cutting with pepsin yields F(ab')$_2$ fragment), and it may be produced through gene recombination technology. The term, "hinge region" is a region comprised in a heavy chain of an antibody, and is present between CH1 and CH2 regions, and means a region functioning to provide flexibility of the antigen-binding region in the antibody.

The anti-ROS1 antibody may be a monoclonal antibody. The monoclonal antibody may be manufactured by a method widely known in the art. For example, it may be manufactured using a phage display method. Otherwise, the anti-ROS1 antibody may be manufactured as a monoclonal antibody derived from a mouse by a common method.

On the other hand, based on the binding ability to ROS1 using a typical ELISA (Enzyme-Linked ImmunoSorbent Assay) format, individual monoclonal antibodies may be screened. Through a functional analysis such as competitive ELISA or a functional analysis such as cell-based assay for assaying molecular interaction for conjugates, the inhibitory activity may be assayed. Then, each affinity (Kd values) to ROS1 may be assayed for selected monoclonal antibody members based on the strong inhibitory activity.

The finally selected antibodies may be used by manufacturing them as not only antibodies in which other portions except for the antigen-binding portion become immunoglobulin antibodies, but also humanized antibodies. The manufacturing method of humanized antibodies is well known in the art.

The patient to which the present invention is applied may be mammals which includes primates including humans, monkeys, etc., and rodents including mice, rats, etc., and the like.

The cancer may be solid cancer or blood cancer, and may be one or more kinds selected from the group consisting of lung cancer (for example, small cell lung cancer, non-small cell lung cancer, lung adenocarcinoma, lung squamous cell carcinoma, etc.), peritoneal carcinoma, skin cancer, skin or eye melanoma, rectal cancer, anal cancer, esophageal cancer, small intestine cancer, endocrine cancer, parathyroid cancer, adrenal cancer, soft tissue sarcoma, urethral cancer, leukemia (for example, chronic or acute leukemia), lymphoma, hepatocellular carcinoma, gastrointestinal cancer, pancreatic cancer, glioblastoma, cervical cancer, ovarian cancer, liver cancer, bladder cancer, liver tumor, breast cancer, colon cancer, colorectal cancer, endometrial or uterine cancer, salivary gland cancer, kidney cancer, liver cancer, prostate cancer, vulva cancer, thyroid cancer, liver cancer, head and neck cancer, brain cancer, osteosarcoma, and the like, but not limited thereto. The cancer may be primary cancer or metastatic cancer.

Meanwhile, the anti-ROS1 antibody or antigen-binding fragment thereof specifically binds to ROS1, particularly, the N-terminal region of ROS1 (for example, the aforementioned epitope region), and therefore using this, ROS1 may be detected or confirmed. Accordingly, other embodiment of the present invention provides a composition for detection of ROS1 comprising the anti-ROS1 antibody or antigen-binding fragment thereof.

Another embodiment provides a detection method of ROS1 comprising treating the anti-ROS1 antibody or antigen-binding fragment thereof to a biological sample; and confirming an antigen-antibody reaction. In the detection method, when the antigen-antibody reaction is confirmed (an antigen-antibody complex is detected), it may be decided (determined) that ROS1 is present in the biological sample. Therefore, the detection method may further comprise determining that ROS1 is present in the biological sample, when the antigen-antibody reaction is detected, after the confirming step. The biological sample may be selected from the group consisting of cells, tissue, body fluid, culture thereof, and the like obtained (isolated) from a mammal, for example, human (for example, cancer patient). By the detection method of ROS1, full-length ROS1 as well as the N-terminal region of ROS1 that is the epitope of the anti-ROS1 antibody may be detected.

In the diagnosis method or detection method of ROS1, the step of confirming an antigen-antibody reaction may be performed by various methods known in the art. For example, it may be measured through common enzyme reaction, fluorescence, luminescence and/or radiation detection, and specifically, it may be measured by the method selected from the group consisting of immunochromatography, immunohistochemistry, enzyme linked immunosorbent assay (ELISA), radioimmunoassay (RIA), enzyme immunoassay (EIA), florescence immunoassay (FIA), luminescence immunoassay (LIA), western blotting, microarray, and the like, but not limited thereto.

In other embodiment, a polypeptide molecule comprising a heavy chain complementarity determining region of the aforementioned anti-ROS1 antibody, a light chain complementarity determining region, or combination thereof; or a heavy chain variable region, a light chain variable region, or combination thereof is provided. The polypeptide molecule may be used for antibody manufacture as a precursor of an antibody, and be also comprised as a constituent of a protein scaffold (for example, peptibody), a bispecific antibody and a multi-specific antibody which have a similar structure to an antibody.

Another embodiment provides a nucleic acid molecule encoding a heavy chain complementarity determining region, a heavy chain variable region or a heavy chain of the anti-ROS1 antibody.

Another embodiment provides a nucleic acid molecule encoding a light chain complementarity determining region, a light chain variable region or a light chain of the anti-ROS1 antibody.

Another embodiment provides a recombinant vector comprising a nucleic acid molecule encoding a heavy chain complementarity determining region, a heavy chain variable region or a heavy chain of the anti-ROS1 antibody, and a nucleic acid molecule encoding a light chain complementarity determining region, a light chain variable region or a light chain of the anti-ROS1 antibody, together with one vector or in separate vectors, respectively.

Another embodiment provides a recombinant cell comprising the recombinant vector.

The term, "vector" may refer to a means for expressing a target gene in a host cell. For example, it includes virus vectors such as a plasmid vector, a cosmid vector, and a bacteriophage vector, a lentivirus vector, an adenovirus vector, a retrovirus vector and an adeno-associated virus vector. The vector which can be used as the recombinant vector may be produced by manipulating plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phages (for example, λgt4AB, λ-Charon, λΔz1 and M13, etc.) or viruses (for example, SV40, etc.) frequently used in the art.

The nucleic acid molecule in the recombinant vector may be operatively linked to a promoter. The term, "operatively linked" means functional binding between a nucleotide expression-regulatory sequence (for example, promoter sequence) and other nucleotide sequence. The regulatory sequence is "operatively linked", thereby regulating transcription and/or translation of other nucleotide sequence.

The recombinant vector may be constructed typically as a vector for cloning or vector for expression. As the vector for expression, common one used for expressing foreign protein in a plant, animal or microorganism in the art may be used. The recombinant vector may be constructed by various methods known in the art.

The recombinant vector may be constructed using a prokaryotic cell or eukaryotic cell as a host. For example, when the vector used is an expression vector, and a prokaryotic cell is used as a host, it is common to comprise a strong promoter which can progress transcription (for example, pL$^\lambda$ promoter, CMV promoter, trp promoter, lac promoter, tac promoter, T7 promoter, etc.), a ribosome binding site for initiation of translation and a transcription/translation terminating sequence. When a eukaryotic cell is used as a host, a replication origin operated in the eukaryotic cell which is comprised in the vector includes f1 replication origin, SV40 replication origin, pMB1 replication origin, adeno-replication origin, AAV replication origin and BBV replication origin, and the like, but not limited thereto. In addition, a promoter derived from a genome of a mammal cell (for example, metallothionein promoter) or a promoter derived from a mammal virus (for example, adenoviral late promoter, vaccinia virus 7.5K promoter, SV40 promoter, cytomegalovirus promoter and tk promoter of HSV) may be used, and it generally has a polyadenylated sequence as a transcription terminating sequence.

Another embodiment provides a recombinant cell comprising the recombinant vector.

The recombinant cell may be obtained by introducing the recombinant vector to an appropriate host cell. As the host cell, any host cell known in the art which is a cell which can stably and continuously clone or express the recombinant vector may be used, and the prokaryotic cell includes for example, *E. coli* JM109, *E. coli* BL21, *E. coli* RR1, *E. coli* LE392, *E. coli* B, *E. coli* X 1776, *E. coli* W3110, *Bacillus* strains such as *Bacillus subtilis* and *Bacillus thuringiensis*, and Enterobacteriaceae strains such as *Salmonella typhimurium*, *Serratia marcescens* and various *Pseudomonas* sp., and the like, and when it is transformed in an eukaryotic cell, as a host cell, enzyme (*Saccharomyces cerevisiae*), an insect cell, a plant cell and an animal cell, for example, HEK293T, Sp2/0, CHO (Chinese hamster ovary) K1, CHO DG44, PER.C6, W138, BHK, COS-7, 293, HepG2, Huh7, 3T3, RIN, MDCK cell line, and the like may be used, but not limited thereto.

The delivery (introduction) of the nucleic acid molecule or recombinant vector comprising it into a host cell may use a delivery method widely known in the art. The delivery method may be, for example, $CaCl_2$) method or electroporation, or the like, when the host cell is a prokaryotic cell, and when the host cell is an eukaryotic cell, microinjection, calcium phosphate precipitation method, electroporation, liposome-mediated transfection method and gene bombardment, and the like may be used, but not limited thereto.

The method for selecting the transformed host cell may be easily conducted according to a method widely known in the art, using a phenotype to be expressed by a selectable marker. For example, when the selectable marker is a specific antibiotic-resistant gene, a transformant may be easily selected by culturing the transformant in a medium containing the antibiotic.

Another embodiment provides a manufacturing method of an anti-ROS1 antibody comprising expressing the nucleic acid molecule or recombinant vector comprising it in a host cell. The manufacturing method may comprise culturing a recombinant cell comprising the recombinant vector and isolating and/or purifying an antibody from a randomly cultured medium.

Herein, an anti-ROS1 antibody or antigen-binding fragment reacting to the N-terminal region of ROS1 is provided, and it was confirmed that an epitope thereof is present near D46-L47-G48-T49 of ROS1 (NP_002935.2; SEQ ID NO: 9). In addition, it was confirmed that an antibody binding to D46-L47-G48-T49 of ROS1 may show cross-reaction with Hsp70s having the same DLGT sequence, and thereby it was confirmed that the specificity of the antibody may be improved by introducing mutation (for example, amino acid substitution) to residues of idiotopes present in HCDR3 of the antibody, and an antibody which accurately distinguishes LDLGT sequence of ROS1 from IDLGT sequence of Hsp70 is provided.

Advantageous Effects

The present specification provides an anti-ROS1 antibody which specifically binds to the N-terminal portion of ROS1, thereby enabling detection of ROS1 (N-terminal or full-length) more accurately and efficiently, and it can be usefully used for research of biological functions of ROS1 and diagnosis of ROS1-related diseases.

BRIEF DESCRIPTION OF THE DRAWINGS

FIG. 1a is a graph showing the amount of 3B20 scFv-rFc fusion protein bound to ROS1.

FIG. 1b is the result of immunoprecipitating by treating lysates of HEK293T cells transfected with lentiviral vectors encoding human ROS1 (full-length) and confirming it by immunoblotting.

FIG. 1c shows the result of immunoprecipitating by treating lysates of HEK293T cells transfected with lentiviral vectors encoding GFP (control; C) or ROS1 (R) with 3B20 antibody and analyzing the isolated protein using MS.

FIG. 2a to FIG. 2c show the result of identification of the 3B20 epitope by alanine substitution mutagenesis in the Gly42 to Ser54 region of human ROS1 protein, and 2a, 2b and 2c show the reactivity to alanine-substituted mutants of 3B20 scFv-Cκ fusion protein, BSA and irrelevant scFv-Cκ fusion protein, respectively.

FIG. 3a and FIG. 3b are the result of measuring the reaction specificity to the recombinant ROS1 (amino acid 37-290)-Cκ fusion protein of 3B20 and 3B20-G1K, and 3a is the result of 3B20 and 3b is the result of 3B20-G1K.

FIG. 3c shows the result of immunoblotting obtained by treating lysates of HEK293T cells transfected with lentiviral vector encoding ROS1 (lane R) or a control vector (lane C; GFP) with 3B20, 3B20-GIK, or ROS1 antibody (Abcam, product number ab5512), respectively.

FIG. 3d is the result showing the result of immunoprecipitating lysates of HEK293T cells transfected with lentiviral vector encoding ROS1 (lane R) or a control vector (lane C; GFP) with 3B20 or 3B20-G1K.

FIG. 4 is the result of immunohistochemistry (IHC) using 3B20-G1K.

DETAILED DESCRIPTION OF THE EMBODIMENTS

Hereinafter, the present invention will be described in more detail by examples, but these are illustrative only and these are not intended to limit the scope of the present invention. It is obvious to those skilled in the art that the examples described below can be modified without departing from the essential gist of the invention.

Reference Example 1. Preparation of the Anti-ROS1 scFv Antibody

Three White Leghorn chickens were immunized and boosted three times with the synthetic peptide (TNLGQQLDLGT PHNLSEGGGC (SEQ ID NO: 16); fusion polypeptide in which the 39$^{th}$ to 56$^{th}$ amino acid regions of ROS1 (GenBank Accession No. NP_002935.2) combined to "GGGC") conjugated to keyhole limpet hemocyanin (Peptron; Daejun, S. Korea). A phage display of a chicken single-chain variable fragment (scFv) antibody library was constructed [See C. F. Barbas, Phage Display: a Laboratory Manual, Cold Spring Harbor Laboratory Press, Cold Spring Harbor, N Y, 2001]. After five rounds of biopanning on the ROS1 synthetic peptide (TNLGQQLD-LGTPHNLSEPGGGC) conjugated to either bovine serum albumin (BSA) or ovalbumin (OVA), the single-chain variable fragment (scFv)-displaying phages were subjected to enzyme-linked immunosorbent assay (ELISA) [See C. F. Barbas, Phage Display: a Laboratory Manual, Cold Spring Harbor Laboratory Press, Cold Spring Harbor, N Y, 2001; S. Park, D. H. Lee, J. G. Park, Y. T. Lee, J. Chung, A sensitive enzyme immunoassay for measuring cotinine in passive smokers, Clin. Chim. Acta 411 (2010) 1238-1242].

As a result, the scFv binding to the synthetic peptide (TNLGQQLDLGTPHNLSEPGGGC; SEQ ID NO: 16) was selected and called 3B20. The amino acid sequences of CDRs and variable regions of 3B20 were summarized in Table 1 below:

TABLE 1

|  | Light Chain | Heavy Chain |
| --- | --- | --- |
| CDR1 | SGGSYGYG (SEQ ID NO: 1) | GFSFSDRGMH (SEQ ID NO: 4) |
| CDR2 | DNTNRPS (SEQ ID NO: 2) | ISGDGYITHYGAAVKG (SEQ ID NO: 5) |
| CDR2 | GSADSSSIAT (SEQ ID NO: 3) | GGGGNIDA (SEQ ID NO: 13) |
| Variable region | LTQPSSVSANLGGTVKITC SGGSYGYG WYQQKAPGSAPVTVIY DNTNRPS DIPSRFSGSKSGSTGTLTITGVQVED EAVYYC GSADSSSIAT FGAGTTLTVL (SEQ ID NO: 23) | AVTLDESGGGLQTPGGTLSLVCKAS GFSFSDRGMH WMRQAPGKGLEYVGA ISGDGYITHYGAAVKG RATISRDNGQSTVRLQLNNLRAEDTATYYCT R GGGGNIDA WGHGTEVIVSSTS (SEQ ID NO: 14) |
| scFv polypeptide | LTQPSSVSANLGGTVKITCSGGSYGYGWYQQKAPGSAPVTVIYDNTNRPSDIPSRFSGS KSGSTGTLTITGVQVEDEAVYYCGSADSSSIATFGAGTTLTVLGQSSRSSGGGGSGGG GSAVTLDESGGGLQTPGGTLSLVCKASGFSFSDRGMHWMRQAPGKGLEYVGAISGDG YITHYGAAVKGRATISRDNGQSTVRLQLNNLRAEDTATYYCTRGGGGNIDAWGHGTE VIVSSTS (SEQ ID NO: 26) | |
| scFv gene | CTG ACT CAG CCG TCC TCG GTG TCA GCA AAC CTG GGA GGA ACC GTC AAG ATC ACC TGC TCC GGG GGC AGC TAT GGC TAT GGC TGG TAC CAG CAG AAG GCA CCT GGC AGT GCC CCT GTC ACT GTG ATC TAT GAC AAC ACC AAC AGA CCC TCG GAC ATC CCT TCA CGA TTC TCC GGT TCC AAA TCC GGC TCC ACG GGC ACA TTA ACC ATC ACT GGG GTC CAA GTC GAG GAC GAG GCT GTC TAT TAC TGT GGG AGT GCA GAC AGC AGC AGT ATT GCT ACA TTT GGG GCC GGG ACA | |

TABLE 1-continued

| Light Chain | Heavy Chain |
|---|---|
| | ACC CTG ACC GTC CTA GGT CAG TCC TCT AGA TCT TCC GGC GGT GGT GGC AGC |
| | TCC GGT GGT GGC GGT TCC GCC GTG ACG TTG GAC GAG TCC GGG GGC GGC |
| | CTC CAG ACG CCC GGA GGA ACG CTC AGC CTC GTC TGC AAG GCC TCC GGG |
| | TTC TCC TTC AGT GAC CGT GGC ATG CAC TGG ATG CGA CAG GCT CCA GGC |
| | AAG GGG CTG GAA TAC GTC GGA GCT ATA AGC GGT GAT GGT TAC ATC ACA |
| | CAC TAT GGG GCG GCG GTG AAG GGC CGT GCC ACC ATC TCG AGG GAC AAC |
| | GGG CAG AGC ACA GTG AGG CTG CAG CTG AAC AAC CTC AGG GCT GAG GAC |
| | ACC GCC ACC TAC TAC TGC ACC AGA GGT GGT GGT GGT AAC ATC GAC GCA |
| | TGG GGC CAC GGG ACC GAA GTC ATC GTC TCC TCC ACT AGT (SEQ ID NO: 27) |

The gene encoding the selected scFv (3B20) was subcloned into modified pCEP4 mammalian expression vectors (V04450; Thermo Fisher Scientific, Rockford, IL, USA), to be expressed a fusion protein in which the scFv was fused with a rabbit antibody fragment crystallizable region Fc (rFc) (scFv(3B20)-rFc fusion protein) [See H. Kim, S. Park, H. K. Lee, J. Chung, Application of bispecific antibody against antigen and hapten for immunodetection and immunopurification, Exp. Mol. Med. 45 (2013) e43.], or a fusion protein in which the scFv was fused with a human kappa light chain constant region (Cκ) (scFv-Cκ fusion protein) [See Y. Lee, H. Kim, J. Chung, An antibody reactive to the Gly63-Lys68 epitope of NT-proBNP exhibits O-glycosylation-independent binding, Exp. Mol. Med. 46 (2014) e114]. The obtained recombinant proteins were purified [See O. Boussif, F. Lezoualc'h, M. A. Zanta, M. D. Mergny, D. Scherman, B. Demeneix, J. P. Behr, A versatile vector for gene and oligonucleotide transfer into cells in culture and in vivo: polyethylenimine, Proc. Natl. Acad. Sci. U.S.A 92 (1995) 7297-7301].

Reference Example 2. ELISA

The ELISA assay was performed with reference to the following document: [H. Kim, S. Park, H. K. Lee, J. Chung, Application of bispecific antibody against antigen and hapten for immunodetection and immunopurification, Exp. Mol. Med. 45 (2013) e43].

Microtiter plates (Costar, Cambridge, MA, USA) were coated with 100 ng of a recombinant ROS1 (37-290 amino acids)-Cκ fusion protein, an irrelevant protein (recombinant PSA (prostate cancer specific antigen; NP_001025218.1))-Cκ fusion protein the synthetic peptide (TNLGQQLD-LGTPHNLSEGGGC)-BSA conjugate or GRP75 (Enzo Life Sciences, Farmingdale, NY, USA) dissolved in coating buffer (0.1 M sodium bicarbonate, pH 8.6). After blocking, 3B20-rFc or 3B20-G1K (the first amino acid G of HCDR3 of 3B20 was substituted to K)-rFc fusion proteins were added. The amounts of bound antibodies were determined using a horseradish peroxidase (HRP)-conjugated goat anti-rabbit IgG antibody (Abcam, Cambridge Science Park, Cambridge, UK) and 2,20-azinobis [3-ethylbenzothiazoline-6-sulfonic acid]-diammonium salt (ABTS) substrate solution (Amresco LLC, Solon, OH, USA). All experiments were performed in triplicate.

For alanine scanning mutagenesis of the 3B20 scFv, microtiter plates (Corning Costar) were coated with 100 ng of the 3B20 scFv-Cκ fusion protein, BSA, or the irrelevant scFv-Cκ fusion protein overnight at 4° ° C. After blocking, the plates were incubated with alanine-substituted ROS1-human antibody Fc (hFc) fusion proteins (each amino acid residue from the 42th amino acid residue (Gly) to the 54$^{th}$ amino acid residue (Ser) was replaced with alanine) or a wild type ROS1-hFc fusion protein. The amount of bound fusion protein was determined using an HRP-conjugated rabbit anti-human IgG Fc antibody (Thermo Fisher Scientific, Rockford, IL, USA).

Reference Example 3. Transduction and Establishment of a ROS1-Expressing Cell Line To generate a pLenti6-human ROS1eDEST construct, pENTR223.1-human ROS1 (Open Biosystems, Huntsville, AL, USA) was transferred into a pLenti6/V5-DEST (Thermo Fisher Scientific, Waltham, MA, USA) lentiviral vector using Gateway recombination cloning technology and Gateway LR Clonase™ (Thermo Fisher Scientific) according to the manufacturer's instructions. To produce a negative control virus, green fluorescent protein (GFP) was also cloned into the same lentiviral vector.

Then, the lentivirus was produced with reference to the following documents: [J. Yin, G. Park, T. H. Kim, J. H. Hong, Y. J. Kim, X. Jin, S. Kang, J. E. Jung, J. Y. Kim, H. Yun, J. E. Lee, M. Kim, J. Chung, H. Kim, I. Nakano, H. S. Gwak, H. Yoo, B. C. Yoo, J. H. Kim, E. M. Hur, J. Lee, S. H. Lee, M. J. Park, J. B. Park, Correction: pigment epithelium-derived factor (PEDF) expression induced by EGFRvIII promotes self-renewal and tumor progression of glioma stem cells, PLOS Biol. 14 (2016) e1002367].

HEK293T cells (American Type Culture Collection, Manassas, VA, USA) were infected with pLenti6-human ROS1-DEST or GFP lentivirus in the presence of 6 mg/ml polybrene [J. Yin, G. Park, J. E. Lee, J. Y. Park, T. H. Kim, Y. J. Kim, S. H. Lee, H. Yoo, J. H. Kim, J. B. Park, CPEB1 modulates differentiation of glioma stem cells via downregulation of HES1 and SIRT1 expression, Oncotarget 5 (2014) 6756-6769]. The transfected cells were cultured in Dulbecco's modified Eagle's medium (DMEM; Welgene, Seoul, S. Korea) supplemented with 10% heat-inactivated fetal bovine serum (GIBCO, Grand Island, NY, USA), 100 U/mL penicillin, 100 mg/mL streptomycin, and 2 mM L-glutamine (GIBCO) in a humidified 5% CO2 atmosphere at 37° C.

Reference Example 4. Immunoblotting

The immunoblotting assay was performed with reference to the following document [H. Kim, S. Park, H. K. Lee, J. Chung, Application of bispecific antibody against antigen and hapten for immunodetection and immunopurification, Exp. Mol. Med. 45 (2013) e43].

Cell lysates were separated using 4-12% Bis-Tris sodium dodecyl sulfate polyacrylamide gel electrophoresis (SDS-PAGE; Thermo Fisher Scientific) and transferred to a nitrocellulose membrane (Whatman, Maidstone, Kent, UK). After blocking, the membrane was probed with the 3B20 scFv-rFc fusion protein (200 ng/mL), the 3B20-G1K scFv-rFc fusion protein (1 mg/mL), anti-ROS1 antibodies (ab5512; Abcam, 69D6; Cell Signaling Technology, Danvers, MA, USA) or an anti-tubulin antibody (Santa Cruz, Dallas, TX, USA). After washing, it was incubated with an HRP-conjugated anti-rabbit IgG antibody (Abcam) or an HRP-conjugated anti-mouse IgG antibody (Pierce Chemical Co., Rockford, IL, USA). The immunoblotting results were visualized using an enhanced chemiluminescence system (Thermo Fisher Scientific).

Reference Example 5. Immunoprecipitation

The immunoprecipitation was performed with reference to the following document: [H. Kim, S. Park, H. K. Lee, J. Chung, Application of bispecific antibody against antigen and hapten for immunodetection and immunopurification, Exp. Mol. Med. 45 (2013) e43].

HEK293T cell lines overexpressing either ROS1 or GFP were lysed in cold lysis buffer [1% Triton X-100, 150 mM NaCl, 50 mM Tris (pH 8.0)] containing 1 mM phenylmethane sulfonyl fluoride (Merck KGaA, Darmstadt, Germany) a protease inhibitor cocktail (Roche), and a phosphatase inhibitor cocktail (Roche). Lysates were incubated with 3B20 scFv or 3B20 scFv-G1K fused to the rFc fusion protein (5 μg/mL) and protein A-conjugated agarose beads (RepliGen, Waltham, MA, USA). After washing, proteins bound to beads were eluted by boiling in NuPAGE LDS Sample Buffer (Thermo Fisher Scientific) and subjected to SDS-PAGE and immunoblotting (See Reference example 4). The eluted proteins separated by SDS-PAGE were visualized using Coomassie Brilliant Blue R250 (Merck). Protein bands about 70 kDa and 260 kDa in the SDS-PAGE gels were excised, and subjected to MS (Mass spectrometry) analysis (See Reference example 9).

Reference Example 6. Preparation of Alanine-Substituted Proteins

For epitope mapping of 3B20 scFv, an alanine scanning mutagenesis assay was performed. A gene encoding ROS1 (the $37^{th}$ to $290^{th}$ amino acids of ROS1) was used as the template and a gene encoding the amino acid sequence in which one of amino acid residues from the 42th amino acid (Gly) through the $54^{th}$ amino acid (Ser) of ROS1 was replaced with alanine by PCR amplification was prepared. The PCR was performed with reference to [Y. Lee, H. Kim, J. Chung, An antibody reactive to the Gly63-Lys68 epitope of NT-proBNP exhibits O-glycosylation-independent binding, Exp. Mol. Med. 46 (2014) e114], and the primers and PCR conditions used for alanine substitution were as follows. At first, after preparatory modification of DNA at 95° C. for 5 minutes, 30 cycles of DNA modification at 95° C. for 30 seconds, combination of primers at 56° C. for 30 seconds, and elongation at 72° C. for 30 seconds were performed, and then it was terminated after incubation for 5 minutes.
Primers

```
Forward primer (5'→3'):
                                            (SEQ ID NO: 17)
GGCCCAGGCGGCCTGTGTAACTAATCTG[GGC/CAG/CAG/CTT/GAC/
CTT/GGC/ACA/CCA/CAT/AAT/CTG/AGT]GAACCGTGT;

reverse primer (5'→3'):
                                            (SEQ ID NO: 18)
GGCCGGCCTGGCCTTCCTCTTGTTGAACTGCTGA
```

(In the forward primer, a codon of the amino acid residues to be substituted to alanine among each codon in the bracket was substituted to the codon encoding alanine, GCC).

The PCR obtained products were purified and subcloned into modified pCEP4 mammalian expression vectors (V04450; Thermo Fisher Scientific) using a restriction enzyme, to be expressed as fusion protein fused with a hFc [S. Park, D. H. Lee, J. G. Park, Y. T. Lee, J. Chung, A sensitive enzyme immunoassay for measuring cotinine in passive smokers, Clin. Chim. Acta 411 (2010) 1238-1242] and purified.

Reference Example 7. Site-Directed HCDR3 Mutagenesis Libraries of the 3B20 scFv

To generate HCDR3 site-directed mutagenesis libraries, the gene encoding 3B20 scFv was used as the template for library construction using the degenerate codon NNK (N is each independently A, C, G, or T; K is G or T) by PCR amplification. The first fragment was PCR amplified using a forward primer (5'-CTGGCTGGTTTCGCTACCGTGGCC-3'; SEQ ID NO: 19) and a reverse primer (5'-TCTGGTGCAGTAGTAGGTGGC-3'; SEQ ID NO: 20); the second fragment was PCR amplified using a forward primer (5' GCCACCACTACTGCACCAGA[GGT/GGT/GGT/GGT/AAC/ATC/GAC/GCA]TGGGGCC AC-3'; SEQ ID NO: 21) and a reverse primer (5'-CGGGTATGCGCCATGGTGATGGTG-3'; SEQ ID NO: 22) (See Reference example 6). The PCR conditions used in the above experiment were as follows. After preparatory modification of DNA at 95° C. for 5 minutes, 30 cycles of DNA modification at 95° C. for 30 seconds, combination of primers at 56° C. for 30 seconds, and elongation at 72° C. for 30 seconds were performed, and then it was terminated after incubation for 5 minutes.

Each codon in the bracket in the forward primer sequence of the second fragment was replaced with NNK. Subsequently, these PCR fragments were purified and subjected to overlap extension PCR. The overlap extension PCR was performed using 100 ng PCR fragments each by after preparatory modification of DNA at 95° C. for 5 minutes, 30 cycles of DNA modification at 95° C. for 30 seconds, combination of primers at 56° C. for 30 seconds, and elongation at 72° C. for 30 seconds, and then it was terminated after incubation for 5 minutes. The obtained overlap extension PCR products were purified and subcloned into a pComb3XSS phagemid vector using Sfi I restriction enzyme and transformed into *Escherichia coli* [See C. F. Barbas, Phage Display: a Laboratory Manual, Cold Spring Harbor Laboratory Press, Cold Spring Harbor, N Y, 2001]. From the output titer plate, phages were rescued from randomly selected colonies and subjected to ELISA [See C. F. Barbas, Phage Display: a Laboratory Manual, Cold Spring Harbor Laboratory Press, Cold Spring Harbor, N Y, 2001].

Reference Example 8. Immunohistochemistry (IHC)

Representative paraffin wax blocks were cut into 4 mm-thick sections and subjected to IHC using an automated immunostainer (Ventana BenchMark XT, Tuscan, AZ, USA). Heat-induced epitope retrieval with Ventana CCI mild reagent was applied and endogenous peroxidase was blocked using 3% $H_2O_2$ for 10 minutes. The slides were incubated with the 3B20-G1K-rFc (300 μg/ml stock; 1:100 dilution) fusion protein for 1 hour. Visualization was done using diaminobenzidine tetrachloride.

Reference Example 9. Mass Spectrometry (MS) Analysis

The in-gel tryptic digestion was performed by cutting the protein band of about 70 kDa and 260 kDa in the SDS-PAGE gel (Reference example 5) [See A. Shevchenko, H. Tomas, J. Havlis, J. V. Olsen, M. Mann, In-gel digestion for mass spectrometric characterization of proteins and proteomes, Nat. Protoc. 1 (2006) 2856-2860]. The cut protein band was destained, and was reduced with 20 mM dithiothreitol, and then was alkylated with 55 mM iodoacetamide. After dehydrating acetonitrile (ACN), proteins were reacted with 12.5 ng/µl modified trypsin (Promega, Madison, WI, USA) (in 50 mM ammonium bicarbonate) at 37° C. overnight and were degraded. Peptides were extracted from gel slices using 50% (v/v) ACN (in 0.1% (v/v) formic acid (FA)). The obtained lysates were dried in Centrivap concentrator (Labconco, Kansas City, MO, USA). The extracted peptide sample was suspended in 0.1% formic acid (in water) and was loaded on EASY-Spray C18 column (75/mm×50 cm×2(m), and it was separated with a 2-35% gradient of 0.1% ofrmic acid (in acetonitrile) at a flow rate of 300 nL/min for 65 minutes. The MS spectrum was recorded in Q-Exactive hybrid quadrupole-Orbitrap mass spectrometer (Thermo Fisher Scientific) interfaced with a nano-ultra-HPLC system (Easy-nLC1000; Thermo Scientific). The obtained MS/MS raw file was converted into mzXMK file using Trans-Proteomic Pipeline (version 4.4), and was analyzed using Sequest (version 27) algorithm in SORCERER (Sage-N Research, Milpitas, CA, USA) platform. Searching was performed using International Protein Index human database (version 3.83, 186578 entries). Full trypsin-sensitive specificity and missed cleavage sites by two were acceptable. The mass tolerances for precursor ions and fragment ions were set to 10 ppm and 1 Da, respectively. The fixed modification for common carbamidomethyl-cysteine and variable modifications for methionine oxidation were used. Using Scaffold (version 4.3.2; Proteome Software, Portland, OR, USA), all the proteins having 99% or higher of ProteinProphet probability (with a minimum of three peptides) and 95% or higher of PeptideProphet probability were confirmed.

Example 1. Reactivity of 3B20 Antibody Against ROS1 and Mass Spectrometry (MS)

A phage display of the scFv library using chicken immunized against the ROS1 synthetic peptide (TNLGQQLD-LGTPHNLSEGGGC, amino acids 39-56 of ROS1) with a complexity of $1.6 \times 10^{10}$ was generated. Through biopanning, a clone, 3B20, which was reactive to both recombinant N-terminus ROS1 (amino acids 37-290)-Cκ fusion protein and the ROS1 synthetic peptide was selected. A recombinant 3B20 scFv-rFc fusion protein was prepared and its reactivity to the recombinant ROS1 protein was evaluated by ELISA.

More specifically, a 96-well microtiter plate was coated with the fusion protein of the recombinant ROS1 (the $37^{th}$ to $290^{th}$ amino acid regions) and kappa invariable region (Cκ) or the synthetic peptide corresponding to the $39^{th}$ to $56^{th}$ amino acids of ROS1 conjugated to bovine serum albumin (BSA), respectively, and after blocking with BSA, 3B20 scFv-rFc fusion protein was added and the amount of the 3B20 scFv-rFc fusion protein combined to ROS1 was measured using an HRP-conjugated anti-rabbit IgG antibody and ABTS solution, thereby evaluating the reactivity of 3B20 scFv-rFc fusion protein. The obtained result was shown in FIG. 1a.

Immunoprecipitation assays were performed using lysates from HEK293T cells transfected with lentiviral vectors encoding human ROS1 (full-length) and 3B20 scFv-rFc fusion protein, with reference to Reference example 5. The immunoprecipitated proteins were subjected to immunoblotting analysis using a commercially available anti-ROS1 antibody reactive to the C-terminal region, and the result was shown in FIG. 1b. More specifically, FIG. 1b is the result of immunoprecipitating the lysates of HEK293T cells transfected with the lentiviral vector encoding human ROS1 (full-length) with (lane 1) or without (lane 2) treating 3B20 scFv-rFc fusion protein (See Reference example 5), and confirming it by immunoblotting using the anti-ROS1 antibody (69D6; Cell Signaling Technology). As shown in FIG. 1b, a band corresponding to a molecular weight of 260 kDa compatible to recombinant ROS1 was clearly visualized.

To investigate the proteins reactive to 3B20 scFv, immunoprecipitation was performed using a 3B20 scFv-rFc fusion protein from HEK293T cells transfected with lentiviral vector encoding human ROS1 (full-length) or GFP (control). Proteins bound to the 3B20 scFv protein were separated by SDS-PAGE. Following electrophoresis, the gel was stained with Coomassie Blue. Bands corresponding to 70 kDa and 260 kDa were excised from the gel and analyzed by liquid chromatography/MS. The obtained result was shown in FIG. 1c, and the list of proteins analyzed in (A) and (B) bands represented by arrows in FIG. 1c was shown in the following Table 2. As expected, ROS1 (accession number: IPI0028965; SEQ ID NO: 9) was detected in a band of 260 kDa.

TABLE 2

|     | Identified Proteins | Accession Number | MW | Transfected Control | Transfected ROS1 |
| --- | --- | --- | --- | --- | --- |
| (A) | Proto-oncogene tyrosine-protein kinase ROS | IPI00288965 | 264 kDa | 0 | 390 |
|     | E3 ubiquitin-protein ligase UBR5 | IPI00026320 | 309 kDa | 215 | 216 |
|     | Isoform 2 of filamin-A | IPI00302592 | 280 kDa | 80 | 97 |
| (B) | 78 kDa glucose-regulated protein (GRP78) | IPI00003362 | 72 kDa | 72 | 193 |
|     | Stress-70 protein, mitochondrial (GRP75) | IPI00007765 (+1) | 74 kDa | 134 | 127 |
|     | Heat shock 70 kDa protein 1A/1B | IPI00304925 | 70 kDa | 102 | 105 |
|     | Isoform 1 of Heat shock cognate 71 kDa protein | IPI00003865 | 71 kDa | 83 | 84 |
|     | Isoform 1 of Myotubularin-related protein 1 | IPI00292601 | 75 kDa | 51 | 43 |

(In Table 2, the numerical values described in transfected control/transfected ROS1 columns mean the number of spectral counting derived from LC-MS/MS data)

As shown in Table 1, the bands around 70 KDa were identified as heat shock proteins including Hsp70, Hsp71, GRP75, and GRP78.

As the result of comparing the amino acid sequences of Hsp70, Hsp71, GRP75 and GRP78 proteins to the amino acid sequence of ROS1 protein, it was found that all of them comprised the amino acid sequence of DLGT in common.

```
ROS1       -------------TNLGQQLDLGTPHNLSEPCIQ
HSP70      -----------MAKAAAIGIDLGTTYSCVGVFQH
HSP71      -----------MSKGPAVGIDLGTTYSCVGVFQR
GRP75      RLVSRRDYASEAIKGAVVGIDLGTTNSCVAVMEG
GRP78      SAARAEEEDKKEDVGTVVGIDLGTTYSCVGVFKN
```

Therefore, we hypothesized that the epitope of the 3B20 scFv is D46-L47-G48-T49 in ROS1.

Example 2. Epitope Mapping of the 3B20 scFv by Alanine Scanning Mutagenesis Assay To further confirm the epitope of the 3B20 scFv, alanine scanning mutagenesis assay was performed using recombinant ROS1 proteins corresponding to amino acids 37-290. First, alanine-substituted ROS1 mutants in which any one of amino acid residues from Gly42 to Ser54 of ROS1 was substituted were prepared. After coating the microtiter plate well with the 3B20 scFv-Cκ fusion protein, BSA or irrelevant scFv-Cκ fusion protein, the plate was incubated with the alanine-substituted ROS1-hFc fusion protein or wild-type ROS1-hFc fusion protein. The amount of the ROS1-hFc fusion protein combined to the plate was measured using the HRP-conjugated anti-hFc antibody and ATBS solution. The obtained result was shown in FIG. 2a (3B20 scFv-Cκ fusion protein coating), 2b (BSA coating) and 2c (irrelevant scFv-Cκ fusion protein coating).

As shown in FIG. 2a, the 3B20 scFv-Cκ fusion protein had the significantly reduced reactivity to L45A mutant, L47A mutant and G48A mutant of ROS1 protein, while it showed the reactivity to other mutants similar to the wild-type ROS1 protein. In addition, as shown in FIGS. 2b and 2c, the BSA or negative control scFv-Fc fusion protein did not react with the ROS1 mutants. Based on this result, it was concluded that three residues, Leu45, Leu47, and Gly48, of ROS1 play critical roles in the binding specificity of the 3B20 scFv. Interestingly, the corresponding residue of Leu45 in Hsp70 was isoleucine. From this finding, monoclonal antibody clones with enhanced specificity to ROS1 were generated by more accurately discriminating LDLGT of ROS1 from IDLGT sequence in Hsp70 by introducing mutations to the 3B20 antibody. As idiotopes of the monoclonal antibody usually harbor HCDR3, it was concluded that this mutation is introduced to HCDR3.

Example 3. Screening of Modified scFv with Enhanced Specificity from the HCDR3 Site-Directed Mutagenesis Library Based on the result of Example 2, to generate monoclonal antibody clones nonreactive to Hsp70 but reactive to ROS1, HCDR3 site-directed mutagenesis libraries were constructed. The HCDR3 region (GGGGNIDA) of 3B20 scFv consists of eight amino acids, and using PCR primers designed to comprise NNK (N is each independently A, C, G or T; K is G or T) codons in every amino acid position of HCDR3, eight NNK phage display libraries were constructed (See Reference example 7). From each library, 48 clones were randomly selected and phage ELISA to recombinant ROS1 and GRP75 was performed. From the first amino acid residue randomized library, one mAb clone reactive only to ROS1 but not to GRP75 was found. As the result of sequence analysis, it was confirmed that the first amino acid residue of HCDR3 region of 3B20 scFv, Glycine (G) had been substituted with lysine (K). The found mAb clone was named 3B20-G1K. The amino acid sequences of CDRs and variable regions of 3B20-G1K were summarized in the following Table 3.

TABLE 3

|  | Light Chain | Heavy Chain |
|---|---|---|
| CDR1 | SGGSYGYG (SEQ ID NO: 1) | GFSFSDRGMH (SEQ ID NO: 4) |
| CDR2 | DNTNRPS (SEQ ID NO: 2) | ISGDGYITHYGAAVKG (SEQ ID NO: 5) |
| CDR2 | GSADSSSIAT (SEQ ID NO: 3) | KGGGNIDA (SEQ ID NO: 6) |
| Variable region | LTQPSSVSANLGGTVKITC SGGSYGYG WYQQKAPGSAPATVIY DNTNRPS DIPSRFSGSKSGSTGTLTITGVQVEDE AVYYC GSADSSSIAT FGAGTTLTVL (SEQ ID NO: 7) | AVTLDESGGGLQTPGGTLSLVCKAS GFSFSDRGMH WMRQAPGKGLEYVGA ISGDGYITHYGAAVKG RATISRDNGQSTVRLQLNNLRAEDTATYY CTR KGGGNIDA WGHGTEVIVSSTS (SEQ ID NO: 8) |
| scFv polypeptide | LTQPSSVSANLGGTVKITCSGGSYGYGWYQQKAPGSAPATVIYDNTNRPSDIPSRFSG SKSGSTGTLTITGVQVEDEAVYYCGSADSSSIATFGAGTTLTVLGQSSRSSGGGGSSG GGGSAVTLDESGGGLQTPGGTLSLVCKASGFSFSDRGMHWMRQAPGKGLEYVGAIS GDGYITHYGAAVKGRATISRDNGQSTVRLQLNNLRAEDTATYYCTRKGGGNIDAWG HGTEVIVSSTS (SEQ ID NO: 24) | |
| scFv gene | CTG ACT CAG CCG TCC TCG GTG TCA GCA AAC CTG GGA GGA ACC GTC AAG ATC ACC TGC TCC GGG GGC AGC TAT GGC TAT GGC TGG TAC CAG CAG AAG GCA CCT GGC AGT GCC CCT GCC ACT GTG ATC TAT GAC AAC ACC AAC AGA | |

TABLE 3-continued

| Light Chain | Heavy Chain |
|---|---|
| | CCC TCG GAC ATC CCT TCA CGA TTC TCC GGT TCC AAA TCC GGC TCC ACG |
| | GGC ACA TTA ACC ATC ACT GGG GTC CAA GTC GAG GAC GAG GCT GTC TAT |
| | TAC TGT GGG AGT GCA GAC AGC AGC AGT ATT GCT ACA TTT GGG GCC GGG |
| | ACA ACC CTG ACC GTC CTA GGT CAG TCC TCT AGA TCT TCC GGC GGT GGT |
| | GGC AGC TCC GGT GGT GGC GGT TCC GCC GTG ACG TTG GAC GAG TCC GGG |
| | GGC GGC CTC CAG ACG CCC GGA GGA ACG CTC AGC CTC GTC TGC AAG GCC |
| | TCC GGG TTC TCC TTC AGT GAC CGT GGC ATG CAC TGG ATG CGA CAG GCT |
| | CCA GGC AAG GGG CTG GAA TAC GTC GGA GCT ATA AGC GGT GAT GGT TAC |
| | ATC ACA CAC TAT GGG GCG GCG GTG AAG GGC CGT GCC ACC ATC TCG AGG |
| | GAC AAC GGG CAG AGC ACA GTG AGG CTG CAG CTG AAC AAC CTC AGG GCT |
| | GAG GAC ACC GCC ACC TAC TAC TGC ACC AGA AAG GGT GGT GGT AAC ATC |
| | GAC GCA TGG GGC CAC GGG ACC GAA GTC ATC GTC TCC TCC ACT AGT (SEQ ID NO: 25) |

Example 4. Enhanced Specificity of 3B20-G1K

To test the specificity of 3B20-GlK, a recombinant 3B20-G1K scFv-Cκ fusion protein was prepared. Then ELISA, immunoblot, and immunoprecipitation analyses were performed in parallel with 3B20 for the prepared fusion protein. More specifically, the microtiter plate well was coated with 100 ng of recombinant ROS1 (amino acids 37-290)-Cκ fusion protein or irrelevant protein-Cκ fusion molecule. After blocking, the 3B20-rFc fusion protein or 3B20-G1K-rFc fusion protein was added to the well in a concentration of 0 to 2000 ng/ml, and the amount of the fusion protein combined to the well was measured by ELISA using the HRP-conjugated anti-rabbit IgG antibody and ABTS solution. The obtained result was shown in FIG. 3a (3B20-rFc fusion protein) and 3b (3B20-G1K-rFc fusion protein), respectively. As shown in FIG. 3a and FIG. 3b, as the result of ELISA, it was observed that 3B20-G1K only reacted with ROS1 and did not react with GRP75, even at a concentration of 2 μg/mL, but 3B20 reacted with GRP75 at a concentration of 50 ng/mL or higher.

In addition, the lysates of HEK293T cells transfected with ROS1 (full-length)-encoding lentiviral vector (lane R) or a control vector (lane C; GFP) were applied for SDS-PAGE, and they were moved to nitrocellulose membranes and were blocked, and then the membranes were probed with a control antibody (ab5512; Abcam) against 3B20, 3B20-GlK or ROS1, thereby performing immunoblotting. The obtained immunoblotting result was shown in FIG. 3c. As shown in FIG. 3c, only one band corresponding to recombinant ROS1 was visualized in the lane loaded with ROS1 gene-transfected HEK293T cell lysates (R lane) (indicated by an arrow), while no band corresponding to the recombinant ROS1 was visualized in control vector-transfected HEK293T cell lysates (lane C).

In addition, immunoprecipitation analysis was performed as follows. HEK293T cells transfected with the ROS1 (full-length)-encoding lentiviral vector (lane R) or a control vector (lane C; GFP) were lysed and were incubated with the 3B20(scFv)-rFc fusion protein and 3B20(scFv)-G1K-rFc fusion protein, and were reacted with protein A agarose beads. After washing, proteins combined to beads were eluted and SDS-PAGE was performed. The proteins combined to beads were visualized by staining with Coomassie Blue. The obtained immunoprecipitation analysis result was shown in FIG. 3d. As shown in FIG. 3d, only a single band corresponding to recombinant ROS1 (indicated by an arrow) was visualized in a lane loaded with 3B20-G1K immunoprecipitate, and the band corresponding to the 3B20-G1K scFv protein (about 55 kDa) was found.

Example 9. IHC Analysis of Human Lung Adenocarcinomas with 3B20-G1K Monoclonal Antibody To evaluate the applicability of 3B20-G1K scFv in the detection of full-length wild type ROS1, immunohistochemistry (IHC) was performed with HEK293T cells transfected with a human ROS1 (full-length)-encoding lentiviral vector (positive control), human lung adenocarcinoma tissues (n=100) (provided by Seoul Metropolitan Government-Seoul National University Boramae Medical Center), and human Non-neoplastic lung tissue (Benign bronchial epithelia and alveolar pneumocytes; provided by Seoul Metropolitan Government-Seoul National University Boramae Medical Center), by the method described in Reference example 8, and the result was shown in FIG. 4.

FIG. 4 (A) is the IHC result for HEK293T cells transfected with the human ROS1 (full-length)-encoding lentiviral vector, and it was found that ROS1 was strongly expressed in both membrane and cytoplasm (×400). FIG. 4 (B) is the IHC result for the human Non-neoplastic lung tissue (Benign bronchial epithelia and alveolar pneumocytes), and expression of ROS1 was not observed (×100). FIGS. 4 (C)-(E) are the IHC results for the human lung adenocarcinoma tissue, and it shows ROS1 expression at low magnification (C; ×200), medium magnification (D; ×200) and high magnification (E; ×400), respectively (the arrow indicates mitotic appearance). FIG. 4 (F) shows the observation pattern at ×400 in the human lung adenocarcinoma tissue, and the ROS1-positive result was confirmed in the cytoplasmic membrane and cytoplasm, and in particular, it can be confirmed that ROS1 expression is enhanced in the membrane.

As shown in FIG. 4, ROS1 gene-transfected HEK293T cell which was used as positive control revealed strong ROS1 expression in the membrane and cytoplasm (A); Benign bronchial epithelia and alveolar pneumocytes that were human non-neoplastic lung tissues were negative for ROS1 (B); Human adenocarcinoma tissues showed a variable degree of ROS1 expression and strong positivity was found in about 10% of the cases. In this case, localization of ROS1 was largely in cytoplasmic membranes, but cytoplasmic expression was also found, especially in strongly positive cases (C-F).

The invention claimed is:

1. An anti-ROS1 antibody or antigen-binding fragment thereof, characterized by binding to a region comprising SEQ ID NO: 11 or SEQ ID NO: 10, in the 39th to 56th region of ROS1 protein (SEQ ID NO: 15), and comprising the following complementarity determining regions (CDRs):

LCDR1 comprising the amino acid sequence of SEQ ID NO: 1 (SGGSYGYG),

LCDR2 comprising the amino acid sequence of SEQ ID NO: 2 (DNTNRPS),

LCDR3 comprising the amino acid sequence of SEQ ID NO: 3 (GSADSSSIAT),

HCDR1 comprising the amino acid sequence of SEQ ID NO: 4 (GFSFSDRGMH),

HCDR2 comprising the amino acid sequence of SEQ ID NO: 5 (ISGDGYITHYGAAVKG), and HCDR3 comprising the amino acid sequence of SEQ ID NO: 6 (KGGGNIDA) or SEQ ID NO: 13 (GGGG-NIDA).

2. The anti-ROS1 antibody or antigen-binding fragment thereof according to claim 1, comprising
a light chain variable region comprising the amino acid sequence of SEQ ID NO: 7 or SEQ ID NO: 23; and
a heavy chain variable region comprising the amino acid sequence of SEQ ID NO: 8 or SEQ ID NO: 14.

3. The anti-ROS1 antibody or antigen-binding fragment thereof according to claim 1, which is:
(1) an anti-ROS1 antibody or antigen-binding fragment thereof comprising the following complementarity determining regions (CDRs):
LCDR1 comprising the amino acid sequence of SEQ ID NO: 1 (SGGSYGYG),
LCDR2 comprising the amino acid sequence of SEQ ID NO: 2 (DNTNRPS),
LCDR3 comprising the amino acid sequence of SEQ ID NO: 3 (GSADSSSIAT),
HCDR1 comprising the amino acid sequence of SEQ ID NO: 4 (GFSFSDRGMH),
HCDR2 comprising the amino acid sequence of SEQ ID NO: 5 (ISGDGYITHYGAAVKG), and
HCDR3 comprising the amino acid sequence of SEQ ID NO: 6 (KGGGNIDA); or
(2) an anti-ROS1 antibody or antigen-binding fragment thereof comprising the following variable regions:
a light chain variable region comprising the amino acid sequence of SEQ ID NO: 7; and
a heavy chain variable region comprising the amino acid sequence of SEQ ID NO: 8.

4. The anti-ROS1 antibody or antigen-binding fragment thereof according to claim 3, wherein the anti-ROS1 antibody or antigen-binding fragment thereof binds to SEQ ID NO: 11 (LDLGT) and does not bind to SEQ ID NO: 12 (IDLGT).

5. The anti-ROS1 antibody or antigen-binding fragment thereof according to claim 3, wherein the anti-ROS1 antibody or antigen-binding fragment thereof specifically binds to ROS1 protein.

6. The anti-ROS1 antibody or antigen-binding fragment thereof according to claim 1, which is:
(1) an anti-ROS1 antibody or antigen-binding fragment thereof comprising the following complementarity determining regions (CDRs):
LCDR1 comprising the amino acid sequence of SEQ ID NO: 1 (SGGSYGYG),
LCDR2 comprising the amino acid sequence of SEQ ID NO: 2 (DNTNRPS),
LCDR3 comprising the amino acid sequence of SEQ ID NO: 3 (GSADSSSIAT),
HCDR1 comprising the amino acid sequence of SEQ ID NO: 4 (GFSFSDRGMH),
HCDR2 comprising the amino acid sequence of SEQ ID NO: 5 (ISGDGYITHYGAAVKG), and
HCDR3 comprising the amino acid sequence of SEQ ID NO: 13 (GGGGNIDA); or
(2) an anti-ROS1 antibody or antigen-binding fragment thereof comprising the following variable regions:
a light chain variable region comprising the amino acid sequence of SEQ ID NO: 23; and
a heavy chain variable region comprising the amino acid sequence of SEQ ID NO: 14.

7. The anti-ROS1 antibody or antigen-binding fragment thereof according to claim 6, wherein the anti-ROS1 antibody or antigen-binding fragment thereof binds to SEQ ID NO: 11 (LDLGT) and SEQ ID NO: 12 (IDLGT).

8. The anti-ROS1 antibody or antigen-binding fragment thereof according to claim 7, wherein the anti-ROS1 antibody or antigen-binding fragment thereof is capable of binding to at least one selected from the group consisting of ROS1 protein, Hsp70, Hsp71, GRP75, and GRP78.

9. The anti-ROS1 antibody or antigen-binding fragment thereof according to claim 1, wherein the anti-ROS1 antibody is an animal antibody, a chimeric antibody or a humanized antibody.

10. The anti-ROS1 antibody or antigen-binding fragment thereof according to claim 1, wherein the antigen-binding fragment thereof is a fusion polypeptide in which scFv, (scFv)2, Fab, Fab', F(ab')2, or scFv of the anti-ROS1 antibody is fused with Fc, or a fusion polypeptide in which scFv is fused with a variable region of a light chain.

11. A pharmaceutical composition for cancer diagnosis, comprising the anti-ROS1 antibody or antigen-binding fragment thereof of claim 1.

12. The composition according to claim 11, wherein the cancer is lung cancer.

* * * * *